United States Patent
Lester et al.

(10) Patent No.: US 7,138,248 B2
(45) Date of Patent: Nov. 21, 2006

(54) METHOD OF INHIBITING INWARD RECTIFIER, G-PROTEIN ACTIVATED, MAMMALIAN, POTASSIUM CHANNELS AND USES THEREOF

(75) Inventors: Henry A. Lester, South Pasadena, CA (US); Norman Davidson, Sierra Madre, CA (US); Paulo Kofuji, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/039,927

(22) Filed: Mar. 16, 1998

(65) Prior Publication Data

US 2002/0052018 A1   May 2, 2002

Related U.S. Application Data

(63) Continuation of application No. 08/614,801, filed on Mar. 7, 1996, now Pat. No. 5,744,324, which is a continuation-in-part of application No. 08/066,371, filed on Mar. 21, 1993, now Pat. No. 5,747,278.

(51) Int. Cl.
    *G01N 33/53* (2006.01)
(52) U.S. Cl. ...................... 435/7.2; 435/69.1
(58) Field of Classification Search ............. 435/7.1, 435/7.2
    See application file for complete search history.

(56) References Cited

OTHER PUBLICATIONS

Adams, M.D., et al., GenBank Acc. No. M78731 (database record).
Sambrook, J., et al., "Synthetic Oligonucleotide Probes," *Molecular Cloning*, 2nd Ed. Cold Spring Harbor: New York, Chapter 11 pp. 11.1-11.60 (1989).
Dascal, N., et al., "Atrial G Protein-Activated K+Channel: Expression Cloning and Molecular Properties," *PNAS, USA*, 90:10235-10239 (1993).
Dascal, N., et al., "Expression of an Atrial G-Protein-Activated Potassium Channel in Xenopus Oocytes," *PNAS, USA*, 90:6596-6600 (1993).
Hemmings, B.A., "α- and β-Forms of the 65 kDA Subunit of Protein Phosphatase 2A Have a Similar 39 Amino Acid Repeating Structure," *Biochem.*, 29:3166-3173 (1990).
Ho, K., et al., "Cloning and Expression of an Inwardly Rectifying ATP-Regulated Potassium Channel," *Nature*, 362:31-38 (1993).
Kubo, Y., et al., "Primary Structure and Functional Expression of a Mouse Inward Rectifier Potassium Channel," *Nature*, 362:127-133 (1993).
Karschin, A., et al., "Heterologously Expressed Serotonin 1A Receptors Couple to Muscarinic K-Channels in Heard," *PNAS, USA*, 88:5694-5698 (1991).
Adams, M.D., et al., "Sequence Identification of 2,375 Human Brain Genes,"0 *Nature*, 355:632-634 (1992).
Lesage, F., et al., "Cloning Provides Evidence for a Family of Inward Rectifier and G-Protein Coupled K+Channels in the Brain," *FEBS. Lett.*, 353:37-42 (1994).
Sakmann, B., et al., "Acetylcholine Activation of Single Muscarinic K+Channels in Isolated Pacemaker Cells of the Mammalian Hear," *Nature*, 303:250-253 (1983).
Yatani, A., et al., "Direct Activation of Mammalian Atrial Muscarinic Potassium Channels by GTP Regulatory Protein $G_K$" *Science*, 235:207-211 (1987).
Kubo, Y., et al., "Primary Structure and Functional Expression of a Rat G-Protein-coupled Mascarinic Potassium Channel," *Nature*, 364:802-806 (1993).
Alrich, R., "Advent of a New Family," *Nature*, 362:107-108 (1993).
Adams, R.L.P., et al., "Biochemistry of the Nucleic Acids," 9th Ed. London: Chapman and Hall, p. 174 (1981).
Krapivinsky, G., et al., "The G-Protein-Gated Atrial K+ Channel $I_{KACh}$ is a Heteromultimer of Two Inwardly Rectifying K+-Channel Proteins," *Nature*, 374:135-141 (1995).

(Continued)

*Primary Examiner*—Michael Pak
(74) *Attorney, Agent, or Firm*—Dorsey & Whitney; Richard F. Trecartin

(57) ABSTRACT

Compositions and methods are provided for producing functional mammalian inward rectifier, G-protein activated potassium channels (Kir3.0 channels). A channel is a multimeric protein comprising one or more Kir3.0 polypeptides, e.g. Kir3.1, Kir3.2, etc., where the polypeptides may be from the same or different species. The functional channel has the distinctive features of an anomalous rectifier, in that it conducts inward but not outward $K^+$ current; it is blocked by low concentrations of extracellular $Cs^+$ or $Ba^{2+}$; and the conductance of the channel does not depend solely on voltage, but on $(E-E_K)$. The ability of the channel to conduct inward $K^+$ current is modulated by G-proteins, particularly G-proteins of the $G_i/G_o$ family. A number of mammalian cell surface receptors activate G-proteins as a consequence of specific ligand binding. The signal transduction from receptor to Kir3.0 channel is therefore coupled through G-protein intermediates.

The functional Kir3.0 channels are useful in drug screening assays directed to modulation of cellular electrophysiology. Nucleic acids encoding Kir3.0 polypeptides are useful for expression of the gene product, and for identification of homologous genes from other species, as well as other members of the same family of proteins. Expression of the nucleic acids in a heterologous cell, e.g. Xenopus oocyte, confers the ability to cause a change in potassium flow in response to G-protein activation.

3 Claims, 6 Drawing Sheets

OTHER PUBLICATIONS

Doupnik, C.A., "The Inward Rectifier Potassium Channel Family," *Current Opinion in Neurobiology*, 5:268-277 (1995).

Kofuji, P., "Evidence that Neuronal G-Protein-Gated Inwardly Rectifying K+Channels are Activated by Gβγ Subunits and Funtion as Heteromultimers," *PNAS, USA*, 92:6542-6546 (1995).

Brown, A.M. "Regulation of Heartbeat by G Protein-Coupled Ion Channels," *Am. J. Physiol.*, 259(6):H1621-H1628 (1990).

Kirsch, G.E. and A.M. Brown, "Trypsin Activation of Atrial Muscarinic K+Channels," *Am. J. Pysiol.*, 26(1):H334-H338 (1989).

Wallace, et al., "Oligonucleotide Probes for the Screening of Recombinant DNA Libraries," *Methods in Enzymology*, 152:432-442.

Duprat, et al., "Heterologous Multimeric Assembly is Essential for K+ Channel Activity of Neuronal and Cardia G-Protein-Activated Inward Rectifiers," *Biochem. Biophys. Res. Comm.*, 212:657-663 (1995).

Lesage, et al., "Molecular Properties of neuronal G-Protein-Activated Inwardly Rectifying K+ Channels," Febs Letters 353:37-42 (1994).

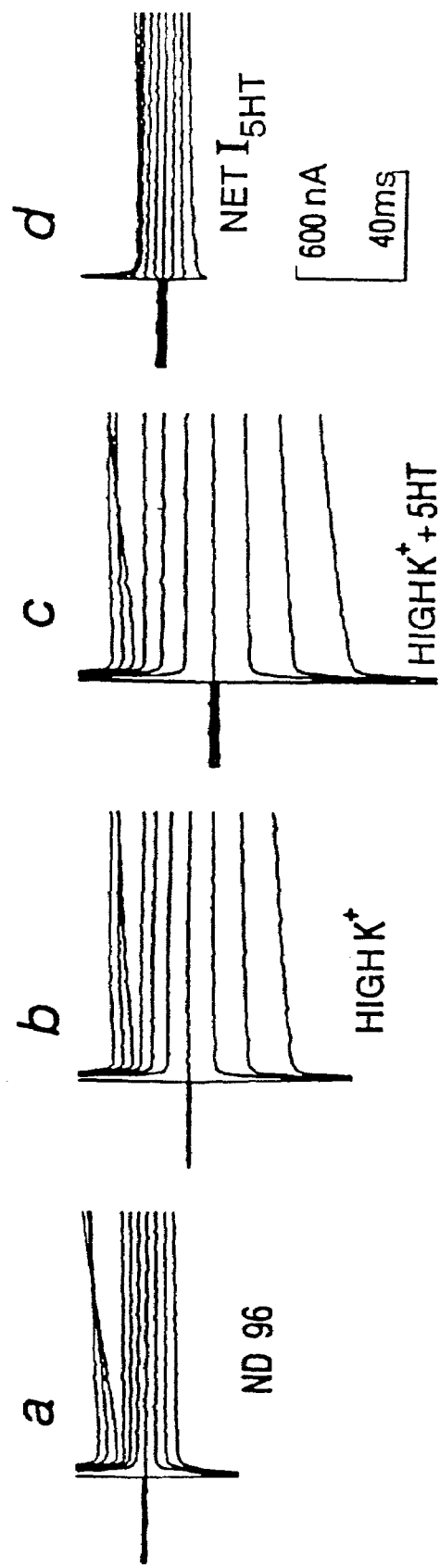

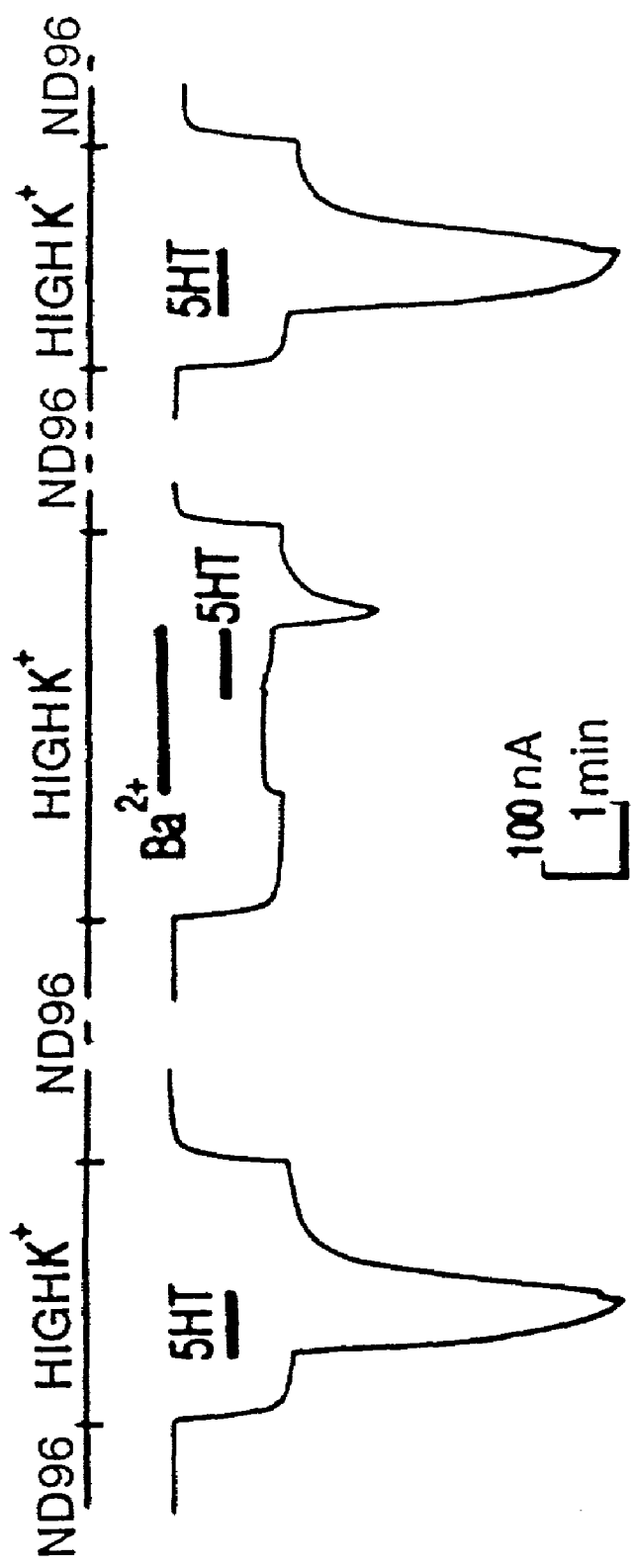

METHOD OF INHIBITING INWARD RECTIFIER, G-PROTEIN ACTIVATED, MAMMALIAN, POTASSIUM CHANNELS AND USES THEREOF

CROSS-REFERENCE TO RELATED APPLICATIONS

This is a continuation division continuation-in-part of application Ser. No. 08/614,801 filed Mar. 7, 1996, now U.S. Pat. No. 5,744,324.

This application is a continuation-in-part of U.S. patent application Ser. No. 08/066,371, filed Mar. 21, 1993 now U.S. Pat. No. 5,747,278.

The invention disclosed herein was made with U.S. Government support under USPHS grants GM29836 and MH49176. The U.S. government has certain rights in this invention.

BACKGROUND

The regulation of heart rate in response to stress, activity, and other stimuli is essential for mammalian survival. While each independent heart muscle has an inherent faculty for independent excitation, the heartbeat is initiated in a specialized group of muscle cells in the sinoatrial node of the heart, which form the pacemaker. The heart is also innervated by nerves that regulate the beat. When these nerves are active, they liberate chemicals such as noradrenaline or acetylcholine from their terminals, and these neurotransmitters affect the cardiac muscles directly. The pacemaker is inhibited by acetylcholine and excited by noradrenaline.

The release of acetylcholine (ACh) opens a $K^+$ channel in the atrium, slowing the rate of depolarization that leads to initiation of the action potential.

This effect is mediated through a G-protein signal transduction pathway, involving a pertussis toxin-sensitive, heterotrimeric G-protein, $G_k$, probably belonging to the $G_i/G_o$ family. Activation of the $K^+$ channel by $G_k$ does not require cytoplasmic intermediates, suggesting direct coupling of one or more G-protein subunits to the channel. However, a long-standing controversy exists as to which subunit couples to the channel. Both purified βγ subunit complex and α subunits of the $G_i/G_o$ family activate the channel in cell free, inside-out patches of atrial myocytes. Activation by the α subunits occurs at lower concentrations than that by βγ, but seems to be less efficient. The relative physiological importance of each pathway, as well as of possible involvement of the arachidonic acid pathway, is unclear.

A similar $K^+$ channel is activated in the atrium by adenosine, ATP and epinephrine, probably also via a G-protein pathway. Furthermore, in nerve cells various 7-helix receptors, such as serotonin 5HT1A, ∂-opioid, $GABA_B$ and somatostatin couple to similar $K^+$ channels, probably through direct activation by G-proteins. The similarity of the channels and signaling pathways in atrium and nerve cells is also shown by the coupling of a neuronal 5HT1A receptor (5HT1A-R) to the atrial channel, through transient expression in myocytes.

By electrophysiological and pharmacological criteria, these $K^+$ channels belongs to a family of inward rectifiers that conduct $K^+$ much better in the inward than the outward direction, are blocked by extracellular $Cs^+$ and $Ba^{2+}$, and are believed to possess a single-file pore with several permeant and blocking ion binding sites. Recently, the primary structures of two mammalian inward rectifier channels have been elucidated by cDNA cloning: an ATP-regulated $K^+$ channel from kidney, and an inward rectifier from a macrophage cell line. Both appear to belong to a new superfamily of $K^+$ channels, with only two transmembrane domains per subunit and a pore region homologous to that of $K^+$, $Ca^{2+}$ and $Na^+$ voltage-dependent channels.

G-protein regulated $K^+$ channels are important for the regulation of heart and nerve function. Determination of their molecular structure and regulation is therefore of great interest. Cloning of the channel protein genes and expression in a heterologous system would allow a molecular approach to investigation and manipulation of these regulatory pathways.

Relevant Literature

The activation of atrial $K^+$ channels by G-proteins is reviewed in Kurachi et al. (1992) *Prog. Neurobiol.* 39:229–246; and Brown and Birnbaumer (1990) *A. Rev. Physiol.* 52:197–213. Logothetis et al. (1987) *Nature* 325: 321–326 and Kurachi et al. (1989) *Pflugers Arch.* 413: 325–327 provide evidence for activation by the βγ subunits. Codina et al. (1987) *Science* 236:442–445 show activation by the α-subunit. Karschin et al. (1991) *P.N.A.S.* 88:5694–5698 demonstrates the coupling of a neuronal receptor to the atrial $K^+$ chanel.

Physiological characterization of the atrial $K^+$ channels is reviewed by Hille, B. (1992) *Ionic Channels of Excitable Membranes*, 2nd edition (Sinauer, Sunderland, Mass.). The role of $Mg^{2+}$ in blocking $K^+$ efflux is discussed in Horie and Irisawa (1987) *Am. J. Physiol.* 253:H210–H214.

The sequence characterization of a mammalian inward rectifier $K^+$ channel is disclosed in Ho et al. (1993) *Nature* 362:31–38; and Kubo et al. (1993) *Nature* 362:127–132. A brief review of these inward rectifying $K^+$ channels may be found in Aldrich (1993) *Nature* 362:107–108.

SUMMARY OF THE INVENTION

Compositions and methods are provided for producing functional mammalian inward rectifier, G-protein activated potassium channels (Kir3.0 channels). The functional channels comprise one or more polypeptides from the Kir3.0 subfamily of inward rectifier potassium channels. The effect that G-protein subunits exert on channel activity is determined by the specific composition of polypeptides in the channel. The functional Kir3.0 channels are useful in drug screening assays directed to modulation of cellular electrophysiology. Nucleic acids encoding Kir3.0 polypeptides are useful for expression of the gene product, and for identification of homologous genes from other species, as well as other members of the same family of proteins.

BRIEF DESCRIPTION OF THE DRAWINGS

FIGS. 2A–D depict that $I_{hk}$ and $I_{5HT}$ are inwardly rectifying $K^+$ currents. (A) Currents evoked by voltage steps from the holding potential of −80 mV to voltages between −140 and 40 mV in 20 mV steps in ND96(a), hK (b), hk in the presence of 5HT (c). Net $I_{5HT}$ (d) was obtained by digital subtraction of (b) from (c). (B) Current-voltage relations of the total membrane current in a representative oocyte in NG 96 (2 mM [$K_{out}$]; □), in 25 mM [$K^+_{out}$]♦); in 75 mM [$K_{out}$]○, and in hK (96 mM [$K_{out}$]; ▲). (C) Current-voltage relation of the net $I_{5HT}$ in the same oocyte as in (B) in 25 mM [$K_{out}$]♦); 75 mM [$K_{out}$]○, and 96 mM [$K_{out}$]▲. (D) The dependence of the reversal potentials of total membrane current ▲and of $I_{5HT}$ ●on [$K_{out}$]. The straight lines represent least square fits to data (mean±SEM, n=3 for each point).

FIGS. 3A–D depict the $Ba^{2+}$ block of $I_{hk}$ and $I_{5HT}$. (A–C) show records taken from the same oocyte at 10 mm intervals. Between the records, the cell was bathed in ND96. 5HT concentration was 4 nM. Note that in (B) 300 *M $Ba^{2+}$ reduces $I_{hk}$ and almost completely blocks $I_{5HT}$. $Ba^{2+}$ and 5HT were washed out simultaneously, and this resulted in an inward current "tail". (D) dose dependence of $BA^{2+}$ inhibition of $I_{hk}$ in native oocytes ○$I_{hk}$ in RNA-injected oocytes ●, $I_{5HT}$ in RNA-injected oocytes. Data are mean±SEM, n=3 to 7 for each point.

DATABASE REFERENCES AND NOMENCLATURE FOR SEQUENCES

Figure 1A:
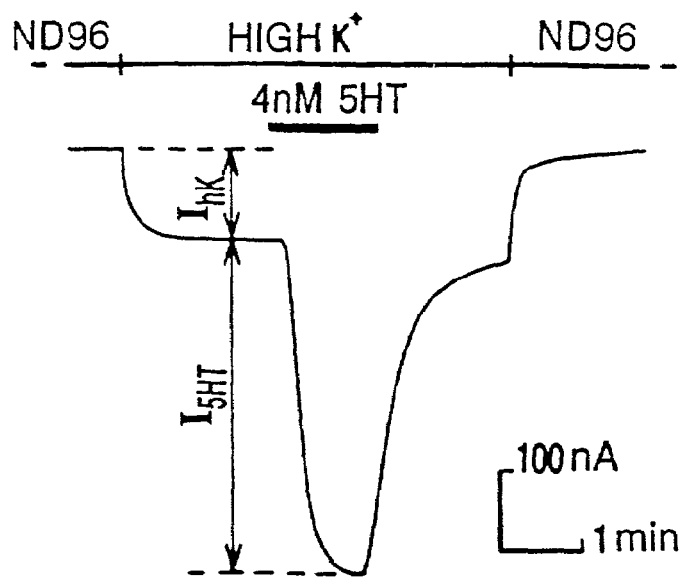
FIGS. 1A–C shows inward currents evoked by high $K^+$, 5HT and ACh in RNA-injected oocytes. (A) $I_{hk}$ and $I_{5HT}$ in an oocyte injected with atrial RNA+5HT1A-R RNA. Holding potential in this and all following figures was −80 mV. (B) Inward currents evoked by ACh (AcCHo) and 5HT in a single oocyte in hK solution. (C) The dependence of $I_{5HT}$ amplitude on 5HT concentration in oocytes of one frog. In each oocyte, the response to one 5HT concentration was tested. Data represent mean±SEM in 4–6 cells at each concentration.

Systematic nomenclature for the family of inward rectifying postassium channel proteins has been proposed by Doupnik et al. (1995) *Curr. Opin. Neur.* 5:268–277. This family is characterized by the presence of only two transmembrane domains per subunit, and a pore region homologous to that of $K^+$, $Ca^{2+}$ and $Na^+$ voltage-dependent channels. As suggested by Doupnik et al., the G-protein regulated members of this family are grouped into the Kir3 subfamily, where "Kir3.0" designates the subfamily of genes and polypeptides, and Kir3.1, 3.2, etc. refer to the specific subfamily members. Other subfamilies include the ATP regulated channels predominantly expressed in the kidney (Kir1.0 subfamily), and the constitutively active, steep inward rectifying Kir2.0 subfamily.

"GIRK1/KGA" and "KGB" are renamed Kir3.1. The Genbank accession numbers for these sequences, from different species, are L25264 (SEQ ID NO:7); U01071 (SEQ ID NO:8); U01141 (SEQ ID NO:9); and D45022 (SEQ ID NO:10).

"GIRK2" is renamed a Kir3.2. The Genbank accession numbers for these sequences, from different species, are U011860 and U24660 (SEQ ID NO:11). "GTRK3" is renamed a Kir3.3. The Genbank accession numbers for this sequence is U11860 (SEQ ID NO:12). "GIRK4", "rcKATP/CIR", "hcKATP" is renamed a Kir3.4. The Genbank accession numbers for these sequences, from different species, are X83584 (SEQ ID NO:13); L35771 (SEQ ID NO:14); X83582(SEQ ID NO:15); and L47208 (SEQ ID NO:16).

A large number of heterotrimeric G-proteins have been characterized. A review of the family and database accession numbers may be found in Watson and Arkinstall (1994) *The G-Protein Linked Receptor FactsBook*, Academic Press, Inc., San Diego, Calif., pp.296–355.

DETAILED DESCRIPTION OF THE INVENTION

Functional mammalian inward rectifier, G-protein activated potassium channels (Kir3.0 channels) are produced by expression of Kir3.0 genes. The multimeric channels vary in their response to G-protein activation, depending on the specific combination of Kir3.0 polypeptides. Drug screening assays directed to modulation of cellular electrophysiology are performed with isolated channels, membrane patches comprising channels, intact cells expressing heterologous channels, etc. Nucleic acids encoding Kir3.0 polypeptides are useful for expression of the gene product, and for identification of homologous genes from other species, as well as other members of the same family of proteins.

As used herein, the term "Kir3.0 channel" designates a functional multimeric protein that comprises one or more Kir3.0 polypeptides, preferably at least two different Kir3.0 polypeptides, e.g. Kir3.1, Kir3.2, Kir3.3, etc., where the polypeptides may be from the same or different species. The functional channel has the distinctive features of an inward rectifier, in that it conducts inward but not outward $K^+$ current; it is blocked by low concentrations of extracellular $Cs^+$ or $Ba^{2+}$; and the conductance of the channel does not depend solely on voltage, but on (E-$E_K$). Characteristic of the Kir3.0 family, the ability of the channel to conduct $K^+$ current is modulated by G-proteins, particularly G-proteins of the $G_i/G_o$ family. It has been found that such modulation may be mediated directly by the G-protein βγ subunit. It will be understood by one of skill in the art that a number of mammalian cell surface receptors activate G-proteins as a consequence of specific ligand binding. The signal transduction from receptor to Kir3.0 channel can therefore be coupled through G-protein intermediates.

The specific combination of Kir3.0 polypeptides in the channel will determine the properties of the channel. As an example, it has been observed that a channel comprised of Kir3.1 and Kir3.2 polypeptides, or of Kir3.1 and Kir3.3 polypeptides, demonstrates a significant enhancement of the G-protein evoked currents. In contrast, a channel comprised of Kir3.2 and Kir3.3 polypeptides shows a decrease in G-protein evoked currents.

As used herein, the term Kir3.0 polypeptide is used to designate a single polypeptide that is capable of associating with other Kir3.0 polypeptides to form a functional Kir3.0 channel as defined above. When a nucleic acid encoding a Kir3.0 polypeptide is introduced into a cell, particularly a Xenopus oocyte, and expressed, it confers a change in the electrophysiology of the cell, such that the cell has an altered ability to conduct $K^+$ current, particularly in response to G-protein activation. Genes encoding Kir3.0 polypeptides can be identified in such a system based on the expression of a single gene, or a combination of genes. The ability of Kir3.0 polypeptides to associate and form multimeric channels in a cell provides a means of identifying genes encoding novel Kir3.0 polypeptides, where a candidate gene may be introduced into a cell comprising a known Kir3.0 gene. A change in the electrophysiology of the cell, as described above, is indicative that the candidate gene encodes a Kir3.0 polypeptide able to partake in multimeric channel formation.

Kir3.0 polypeptides may also be characterized by sequence similarity to known members of the Kir3.0 family. SEQ ID NO:2 describes an exemplary Kir3.1 polypeptide, of rat origin. Within a species, various members of the Kir3.0 gene family will usually have at least about 50% amino acid sequence identity, more usually at least about 60%, and may be as high as 70 to 80%. Between mammalian species, the homologous Kir3.0 polypeptides, e.g. human and rat Kir3.1, etc., have a high degree of similarity, usually at least about 75% amino acid sequence identity, more usually at least about 85% sequence identity, and may be as high as 90% sequence identity, particularly in the conserved transmembrane and pore forming regions.

For convenience in experimental manipulation and drug screening assays, the Kir3.0 channel may be assembled in an expression host cell. As used herein, an expression host cell is a cell, preferably a eukaryotic cell having substantially no endogenous Kir3.0 channels. The expression host will have introduced into it one or more different exogenous nucleic acid(s) encoding one or more Kir3.0 polypeptides, preferable at least two polypeptides. Such exogenous nucleic acids will be capable of constitutive or inducible expression of the Kir3.0 nucleic acid(s) in the host cell. Where two or more polypeptides are present, the genes encoding Kir3.0 polypeptides may be on a single vector or DNA molecule, or may be present on separate molecules. The expression of the exogenous nucleic acid causes an altered ability to conduct $K^+$ current in the expression host cell, particularly in response to G-protein activation. For example, nucleic acids encoding one or more mammalian Kir3.0 polypeptides can be inserted into a host cell, e.g. Xenopus oocyte; yeast; mammalian immortalized cell line or primary cell culture; plant cell; etc. by transfection, injection, transduction, etc. Expression of the nucleic acid produces Kir3.0 polypeptides, which will assemble into a channel in the membrane of the host cell. It has been found in some cases that the heterologous Kir3.0 polypeptide will assemble with polypeptides of the heterologous host cell to form a hybrid channel. Cell surface receptors, such as muscarinic receptors, serotonin receptors, etc., and G-proteins may additionally be introduced into the heterologous host cell. A functional heterologous channel will regulate inward $K^+$ current in response to the presence of exogenous or endogenous activated G-proteins.

The Kir3.0 channels in homologous or heterologous cells are useful in the study of cell electrophysiology, including but not limited to neural and cardiac cells, particularly G protein linked responses, such as those coupled to acetylcholine and serotonin receptor binding. Of particular interest are in vitro drug screening assays. Screening assays are provided to identify drug candidates that specifically alter Kir3.0 channel activity either directly or indirectly by modulating receptors, G-proteins, channels or the interactions among these elements. Novel binding agents include specific antibodies, natural or non-natural binding agents identified in screens of chemical libraries, analogs of acetylcholine, G proteins, etc. Areas of investigation include the development of cardiovascular, neurologic endocrine and gastrointestinal treatments.

Nucleic acid molecules are provided that encode individual polypeptides capable of forming a Kir3.0 channel. The subject polypeptide may be any one of Kir3.1 (for purposes of continuity referred to hereafter as Kir3.1/KGA), Kir3.2, Kir3.3, Kir3.4, etc. The orgin of the nucleic acid may be any mammalian species, e.g. human, murine, primate, bovine, equine, canine, feline, ovine, porcine, etc.

"Kir3.0 genes" shall be intended to mean the nucleotide sequences encoding specific Kir3.0 polypeptides, as well as adjacent 5' and 3' non-coding nucleotide sequences involved in the regulation of expression of the protein encoded by the genes, and will include up to about the length of the mature mRNA. Also included is the corresponding genomic sequence, and may include up to 1 kb of flanking genomic DNA at either the 5' or 3' end of the coding region. These non-coding sequences include termination sequences, introns, regulatory protein binding sequences, translational regulatory sequences, and the like.

The nucleic acid compositions of the subject invention encode all or a part of the subject Kir3.0 polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, more usually at least 18 nt. Preferably fragments will encode a functional epitope or domain. The sequence providing for a functional epitope can be determined by expression of the sequence, and assaying for reactivity of the expression product with specific antibodies by conventional immunoassay, or by assaying for the ability of the fragment to create a polypeptide capable of assembling into a functional Kir3.0 channel.

The DNA sequences may be obtained in substantial purity, and will be obtained as a sequence other than a sequence of an intact chromosome. Usually, the DNA will be obtained substantially free of other nucleic acid compounds which do not include a Kir3.0 sequence or fragment thereof, generally being at least about 50%, usually at least about 90% pure and are typically "recombinant", i.e. flanked by one or more nucleotides with which they are not normally associated with on a natural chromosome.

The subject nucleic acids may be used in a variety of ways. They may be used as probes for identifying other Kir3.0 genes. Homologous sequences and related members of the Kir3.0 gene family are those with substantial sequence similarity to the subject sequences, as previously described. Algorithims for sequence analysis are known in the art, and include BLAST, described in Altschul et al. (1990) *J Mol Biol* 215:403–10; ADVANCE and ADAM, described in Torelli and Robotti (1994) *Comput Appl Biosci* 10:3–5; and FASTA, described in Pearson and Lipman (1988) *P.N.A.S.* 85:2444–8.

Such homologous or related nucleic acid sequences are detected by hybridization under low stringency conditions, for example, at 50° C. and 10×SSC (0.9 M saline/0.09 M sodium citrate) and remain bound when subject to washing at 55° C. with 1×SSC. The high degree of similarity between Kir3.0 homologs allows the use of relatively stringent hybridization conditions, as known in the art. For example, see Sambrook et al. *Molecular Cloning* (Cold Spring Harbor, N.Y., 1989). By using probes, particularly labeled probes of DNA sequences, one may be able to isolate homologous genes, which may be then used for identifying members of the Kir3.0 family in other species. By probes is intended a single stranded oligonucleotide of at least about 12 nt in length, more usually at least about 15 nt, and preferably at least about 18 nt, characterized by the ability to hybridize under low stringency conditions to Kir3.0 genes. The term "unique" as used herein defines a nucleic acid molecule that does not contain known genomic repeated sequences, including but not limited to Alu sequences.

Various methods are known in the art for identification of nucleic acids having sequence similarity, based on the ability of single stranded nucleic acids, e.g. DNA to form a double stranded complex. A sample may be screened for the presence of nucleic acids capable of forming double stranded complexes with a Kir3.0 probe, particularly under low stringency conditions. "Sample" as used herein includes but is not limited to genomic libraries, cDNA libraries, nucleic acid molecule extracts from tissue, or nucleic acid molecule extracts from cell culture. After complex formation, the other nucleic acid molecule is isolated by methods known in the art. Methods include the polymerase chain reaction (PCR) or reverse transcriptase PCR (RT-PCR), where two probes from the subject nucleic acids sequence are used to amplify a region of the sample DNA or cDNA. PCR may also be performed with a single Kir3.0 probe, and a second oligonucleotide complementary to a known genomic repeat sequence. Alternatively, northern or southern blots are useful in identifying bands, colonies, plaques, etc. comprising nucleic acids capable of hybridizing to a Kir3.0 probe. Generally the Kir3.0 probe will be labeled with a detectable marker, e.g. $^{32}P$, $^{35}S$, biotin, FITC, etc. when used in a northern or southern blot.

The subject nucleic acids may also be used to identify the expression of Kir3.0 genes in a biological specimen. The manner in which one probes cells for the presence of particular nucleotide sequences, particularly as genomic DNA, is well-established in the literature and does not require elaboration here. Conveniently, a biological specimen is used as a source of mRNA. The mRNA may be amplified by polymerase chain reaction using primers specific for the subject DNA sequences. Alternatively, the mRNA sample is separated on gel electrophoresis and then probed using Northern blotting with a fragment of the subject DNA as a probe. Other techniques may also find use. Detection of mRNA having the subject sequence is indicative of Kir3.0 expression in the sample.

The subject nucleic acid sequences may be modified for a number of purposes, particularly where they will be used intracellularly, for example, by being joined to a nucleic acid cleaving agent, e.g. a chelated metal ion, such as iron or chromium for cleavage of the gene; as an antisense sequence; or the like. Modifications may include replacing oxygen of the phosphate esters with sulfur or nitrogen, replacing the phosphate with carboxamide, phosphoramide, etc.

The DNA sequence may encode amino acid sequences that differ from the native sequence of a Kir3.0 polypeptide, but that do not produce functional changes in the Kir3.0 polypeptide. The sequence may encode polypeptide analogs, fragments or derivatives of substantially similar polypeptides that differ from the naturally-occurring forms in terms of the identity of location of one or more amino acid residues (deletion analogs containing less than all of the residues specified for the protein, substitution analogs wherein one or more residues are replaced by other residues and addition analog wherein one or more amino acid residues is added to a terminal or medial portion of the polypeptides) and which share some or all properties of naturally-occurring forms. These sequences include the incorporation of preferred codons for expression in non-mammalian host cells; the provision of sites for cleavage by restriction endonuclease enzymes; the addition of promoters operatively linked to enhance RNA transcription; and the provision of additional initial, terminal or intermediate DNA sequences that facilitate construction of readily expressed vectors.

For expression, the DNA sequences may be inserted into an appropriate expression vector, where the native transcriptional initiation region may be employed or an exogenous transcriptional initiation region, i.e. a promoter other than the promoter which is associated with the gene in the normally occurring chromosome. The promoter may be introduced by recombinant methods in vitro, or as the result of homologous integration of the sequence into a chromosome. A wide variety of transcriptional initiation regions are known for a wide variety of expression hosts, where the expression hosts may involve prokaryotes or eukaryotes, particularly E. coli; B. subtilis; yeast cells; mammalian cells; e.g. Cos cells, HeLa cells, L(tk–), primary cultures; insect cells; Xenopus laevis oocytes; and the like. Generally a selectable marker operative in the expression host will be present. The promoter may be operably linked to the coding sequence of the genes of interest so as to produce a translatable mRNA transcript. Expression vectors have convenient restriction sites located near the promoter sequence so as to provide for the insertion of nucleic acid sequences encoding heterologous proteins. The promoters in suitable expression vectors may be either constitutive or inducible. Expression vectors for the production of fusion proteins, where the exogenous fusion peptide provides additional functionality, i.e. increased protein synthesis, stability, reactivity with defined antisera, an enzyme marker, e.g. β-galactosidase, etc.

Expression vectors may also be used to produce mRNA encoding a Kir3.0 polypeptide. The mRNA may be isolated, and used for synthesis of the polypeptide by injecting the RNA molecules into Xenopus oocytes and culturing the oocytes under conditions that are well known to an ordinary artisan.

The subject nucleic acids are used to identify nucleic acids encoding receptors and G-proteins that modulate the activity of Kir3.0 channels by activating or deactivating the channel. As previously described, such methods may also be used to identify genes encoding novel Kir3.0 polypeptides as well. A candidate nucleic acid or library of nucleic acids may be introduced into an expression host cell comprising a Kir3.0 channel, and the host cell screened for a change in the Kir3.0 channel activity. The candidate nucleic acid or library of nucleic acids may be selected from a variety of sources, including cDNA expression constructs operable in the host cell or mRNA transcribed in vivo or in vitro and subsequently introduced into the host cells. Pools of different nucleic acids may be tested, where positive pools are then used to generate smaller pools or individual clones. Nucleic acids that give a positive signal for modulation of Kir3.0 channel activity are then isolated and characterized as to the nucleic acid sequence and structure. The change in channel activity may be the result of expression of the candidate nucleic acid directly, or a known activating agent may be added to the cells to effect a change in channel activity.

A candidate nucleic acid encoding a putative receptor or G protein that interacts with the subject channels may be tested for its ability to modulate Kir3.0 channel activity. The candidate nucleic acid is introduced into an expression host in conjunction with a Kir3.0 expression construct of one or more Kir3.0 polypeptides, preferably at least two polypeptides. The expression host is contacted with a known G-protein associated receptor activator, where an increase in Kir3.0 channel conductance indicates activation of the channel, and a decrease in conductance indicated inhibition of the channel.

Expression cassettes may be prepared comprising a transcription initiation region, which may be constitutive or inducible, the gene encoding the subject methyltransferase or fragment thereof, and a transcriptional termination region. Of particular interest is the use of sequences which allow for the expression of functional epitopes or domains, usually at least about 24 nucleotides in length, more usually at least about 48 nucleotides in length, and up to the complete open reading frame of the gene. After introduction of the DNA, the cells containing the construct may be selected by means of a selectable marker, the cells expanded and then used for expression.

The expression cassettes may be introduced into a variety of vectors, where the vectors will normally be characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence will be provided for the replication of the plasmid, which may be a low- or high-copy plasmid. A wide variety of markers are available for selection, particularly those which protect against toxins, more particularly against antibiotics. The particular marker that is chosen will be selected in accordance with the nature of the host, where in some cases, complementation may be employed with auxotrophic hosts, e.g. bacteria, yeast. Introduction of the DNA construct may be by any convenient means, e.g. conjugation, calcium-precipitated DNA, electroporation, fusion, transfection, infection with viral vectors, etc.

With the availability of the protein in large amounts by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to 100% pure. By pure is intended free of other proteins, as well as cellular debris.

The polypeptide may be used for the production of antibodies. Antibodies may be prepared in accordance with conventional ways, where the expressed polypeptide or protein is used as an immunogen, by itself or conjugated to known immunogenic carriers, e.g. KLH, BSA, etc. Various adjuvants may be employed, as appropriate. For monoclonal antibodies, after one or more booster injections, the spleen of the immunized animal is isolated, the splenocytes immortalized, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. The antibodies may find use in diagnostic assays for detection of the presence of Kir3.0 channels in patient samples.

By providing for the production of large amounts of Kir3.0 polypeptides and channels, one can identify ligands or substrates which bind to, or modulate the action of Kir3.0 channels. The subject Kir3.0 channels, polypeptides or functional domains thereof are used to screen for agonists or antagonists that modulate the $K^+$ channel activity, by increasing or decreasing the evoked $K^+$ current. In this way, drugs may be identified that can alter the electrophysiology of cells comprising Kir3.0 channels, including atrial, neural, vascular smooth muscle, endothelial, pancreatic and other cells. Of particular interest are screening assays for agents that have a low toxicity for human cells. A wide variety of assays may be used for this purpose, including whole cell or single channel current quantitation in response to stimulus, patch clamping, labeled in vitro protein-protein binding assays, electrophoretic mobility shift assays, immunoassays for protein binding, and the like.

In a preferred embodiment, a whole cell or single channel current will be quantitated in the presence of a candidate pharmacological agent. The assay will include contacting a cell into which has been introduced a functional Kir3.0 channel with a candidate pharmacological agent, and detecting any change in channel conductance. An increase in inward $K^+$ channel conductance indicates channel activation, while a decrease indicates that the agent is a channel inhibitor.

The term "agent" as used herein describes any molecule, protein, or pharmaceutical with the capability of directly or indirectly altering ion channel conductance by affecting second messenger systems, receptors, G-proteins, interactions among the elements, or the ion channel directly. Agents include but are not limited to serotonin, neurotropin, enkephalins, dopamine, arachidonic acid, cholera toxin, and pertussis toxin. Generally a plurality of assay mixtures are run in parallel with different agent concentrations to obtain a differential response to the various concentrations. Typically, one of these concentrations serves as a negative control, i.e. at zero concentration or below the level of detection.

The term "activators" as used herein defines any agent which activates a Kir3.0 channel, G-protein associated receptor or G-protein. The term "activates" as used herein is applied to both G-protein associated receptors and ion channel conductance and in terms of G-protein associated receptors defines the state of the receptor wherein it initiates release of a G-protein subunit which in turn initiates a cellular response. In terms of the ion channel conductance "activates" defines the state of the channel wherein the channel increases conductance. The term "deactivates" as used herein defines the state of the channel wherein the channel is initiated to decrease conductance or is incapable of conductance under conditions when the channel normally conducts ions across a membrane. The term "agonist" as used herein defines an agent that initiates activation of ion channel conductance or initiates activation of a second messenger system. The term "antagonist" as used herein defines an agent that initiates deactivation of ion channel conductance or initiates deactivation of a second messenger system.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon, heterocyclic or carbocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Various techniques for performing screening assays are known in the art. For example, a screening assay may utilize one or more molecules conjugated to a label, where the label can directly or indirectly provide a detectable signal. Various labels include radioisotopes, fluorescers, chemiluminescers, enzymes, specific binding molecules, particles, e.g. magnetic particles, and the like. A mixture of the components are added to the assay sample, and the binding of candidate agents to the subject channels, receptors or G proteins is detected. Alternatively, a host cell expressing a Kir3.0 channel is combined with a candidate agent under conditions that induce a change in K+ current.

When an agent is identified that has a desired pharmacological activity, it may be used for prophylactic, therapeutic or experimental purposes. Such agents find use in investigating the interactions of inward K+ channels with surface membrane receptors, G-proteins and second messenger systems. For therapeutic use. the agent may be administered in a physiologically acceptable carrier to a host. The agents may be administered in a variety of ways, orally, parenterally e.g. subcutaneously, intraperitoneally, intravascularly, intralingually, topically, etc. Depending upon the manner of introduction, the compounds may be formulated in a variety of ways, where the concentration of therapeutically active compound in the formulation may vary from about 0.1–100 wt. %.

For convenience, a kit may be provided having the components necessary to perform the subject screening assays. Such a kit may contain at least one expression vector comprising a Kir3.0 gene. Usually at least two Kir3.0 genes will be included, which may be on one vector or two vectors. The kit may further comprise agents for the detection of $K^+$ current change, and agents having a known positive or negative effect on activity of Kir3.0 channels or receptors associated therewith.

The following examples are offered by way of illustration and not by way of limitation.

EXPERIMENTAL

Isolation of a cDNA Encoding Kir3.1/KGA

A cDNA plasmid library was made from 19-day-old rat atrial mRNA. The library was linearized and amplified by polymerase chain reaction using primers complementary to sequences flanking the cDNA insert. cRNA was synthesized in vitro from the T7 promoter and microinjected into *Xenopus laevis* oocytes. Electrophysiological recordings identified an inward rectifier, G-protein activated, potassium channel.

Materials and Methods

Preparation of RNA and oocytes. Total RNA was extracted from atria and ventricles of 19–21 day old rats of both sexes using the procedure of Chomczinski and Sacchi (1987) *Anal. Biochem.* 162:156–159. Poly (A) RNA was separated on an oligo-dT cellulose column (type 3, Collaborative Biochemical Products). Ventricle poly(A) RNA was fractionated by centrifugation (18 h, 30,000 g, 4° C.) on a linear 5%–25% sucrose gradient. *Xenopus laevis* oocytes were prepared as previously described (Dascal & Lotan (1992) in *Methods in Molecular Biology, v.* 13: *Protocols in Molecular Neurobiology*, eds. Longstaff & Revest). and injected with either 50–120 ng/oocyte poly(A) RNA, 120–200 ng/oocyte total RNA, or 35 ng/oocyte fractionated poly(A) RNA. In most cases, 5HT1A-R RNA (5–20 ng/oocyte) was co-injected with atrial or ventricle RNA. Final volume of the injected RNA solution was 50 nl. The oocytes were incubated for 3–7 days in the NDE solution (ND96 (see below) containing 1.8 Mm $CaCl_2$ and supplemented with 2.5 Mm Na-pyruvate and 50 μg/ml gentamicin). Occasionally, either 2.5–5% heat-inactivated horse serum or 0.5 mM theophylline were added to the NDE solution. Incubation of oocytes in pertussis toxin (PTX; List Biochemicals) was done in NDE solution without the addition of pyruvate, serum or theophylline. cDNAs of 5HT1A receptor (Karschin et al. (1991) *P.N.A.S.* 88:5694–5698) and $G_{i2}a$ (a gift from M. I. Simon, Caltech) in pBluescript were linearized, and RNA was synthesized in vitro as described (Dascal and Lotan, supra.).

Electrophysiological recordings were performed using the two electrode voltage clamp method with the Dagan 8500 amplifier (Dagan Instruments, Minneapolis) as described (Dascal et al. (1986) *Mol. Brain Res.* 1:201–209). The oocytes were usually kept in the ND96 solution: 96 mM NaCl/2 mM KCl/1 mM $MgCl_2$/1 mM $CaCl_2$/5 mM Hepes, pH=7.5. Most measurements were done in the high $K^+$ solution (hK): 96 mM KCl/2 mM NaCl/1 mM $MgCl_2$/1 mM $CaCl_2$/5 mM Hepes, pH=7.5. Solutions containing intermediate concentrations of $K^+$ were made by substituting $K^+$ for $Na^+$. Solution exchange and drug application were done by superfusing the cell placed in a 0.5 ml chamber. GDP-β-S (trilithium salt; Sigma) was injected by pressure (Dascal et al. supra.). Stimulation, data acquisition, and analysis were performed using pCLAMP software (Axon Instruments, Foster City, Calif.).

RESULTS

To express the KG channel, the oocytes were injected with atrial total or poly(A) RNA. In order to avoid the possibility that a low level of expression of the muscarinic receptor will make undetectable even a well-expressed KG channel, atrial RNA was usually supplemented with mRNA coding for the serotonin-5HT1A receptor (5HT1A-R); oocytes injected with this RNA mixture will be termed RNA-injected oocytes throughout the paper. When expressed in atrial myocytes, the 5HT1A-R efficiently coupled to the KG channel normally existing in these cells (Karschin et al. supra.), and it was expected to do so in the oocytes.

Four to 5 days after RNA injection addition of 10 μM ACh or 1–2μM 5HT to the ND96 bath solution did not cause any significant change in membrane current. Therefore, the effects of ACh and 5HT were tested in a high potassium (hK) solution with 96 mM $K^+$ and 2 mM $Na^+$. In this solution, the $K^+$ equilibrium potential ($E_K$) is close to 0 mV, and this enables inward $K^+$ current flow through inwardly rectifying K channels at negative holding potentials (–80 mV was routinely used in this study).

Changing ND 96 to the hK solution was accompanied by the development of an inward current that reached a steady level within 0.5–1 min ($I_{hK}$; FIG. 1A). $I_{hK}$ was also observed in native (not injected with any RNA) oocytes, or in oocytes injected with 5HT1A-R RNA alone, but it was always larger in RNA-injected oocytes (P<0.001,two-tailed t-test; Table 1).

Table 1

Inward currents evoked by high $K^+$ and by 5HT. The entries are inward currents in nA shown as mean±SEM (n), measured at –80 mV in the hK solution. 5HT concentration ranged in different experiments from 100 nM to 2 μM.

| Injected RNA | $I_{hK}$ | $I_{5HT}$ |
| --- | --- | --- |
| None (native oocytes) | 72 ± 6 (34) | 0 (18) |
| 5HT1A-R | 54 ± 4 (11) | 0 (12) |
| Atrial + 5HT1A-R | 123 ± 8 (55) | 290 ± 43 (55) |

Figure 1B:
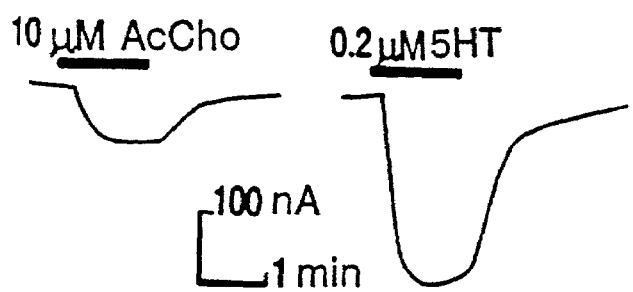

In RNA-injected oocytes, application of 5HT or ACh in hK solution induced an inward current ($I_{5HT}$) that subsided upon washout of the transmitter (FIGS. 1A, B). The response to ACh was usually smaller than to 5HT when measured in the oocytes of the same frog (FIG. 1B). Thus, in oocytes of one frog $I_{5HT}$ was 1102±84 nA (n=6), whereas the ACh response was 382±45 nA(n=6). $I_{5HT}$ tended to decrease on repeated applications of 5HT, and this could be overcome by increasing the intervals between applications to 10 min or more, suggesting the presence of a desensitization process. $I_{5HT}$ and an increased (in comparison with native oocytes) $I_{hK}$ were also observed in oocytes injected with ventricle poly (A) RNA+5HT1A-R RNA, but the $I_{5HT}$ was about 20 times smaller than with atrial poly(A) RNA (not shown). 5HT had no effect in oocytes injected with atrial RNA without the 5HT1A-R RNA (n=4) or with 5HT1A-R RNA alone, or in native oocytes (Table 1).

Figure 1C:
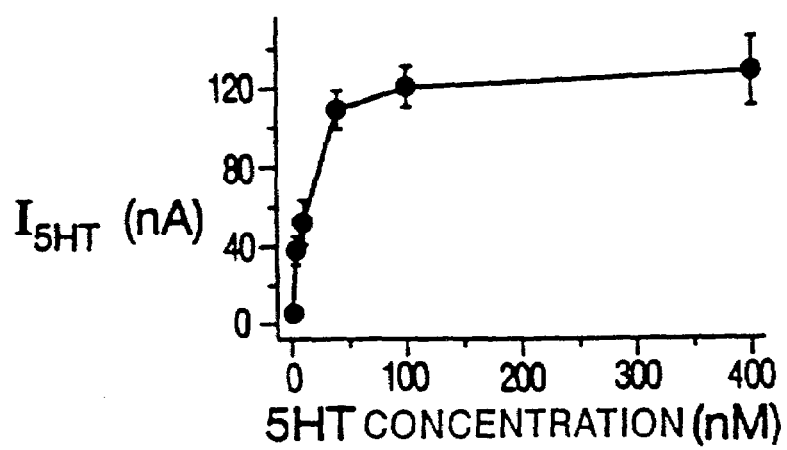

The 5HT dose-response curve showed saturation at about 100 nM and a half-maximal response at about 15 nM (FIG. 1C), which is characteristic of the 5HT1 receptor class (Hoyer & Schoeffer (1991) *J. Recept. Res.* 11:197–214). A similar current was evoked by a selective 5HT1A agonist, 8-OH DPAT (8-OH-2(D1-n-(propylamino)-tetralin).

Figure 2B:
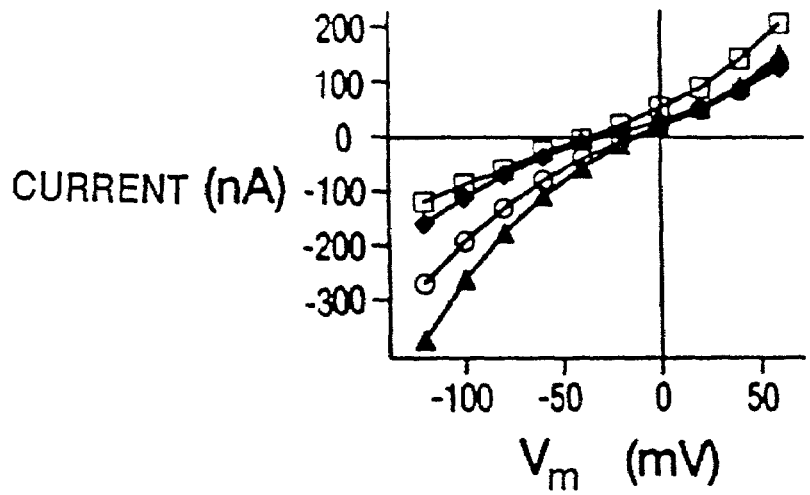
Figure 2C:
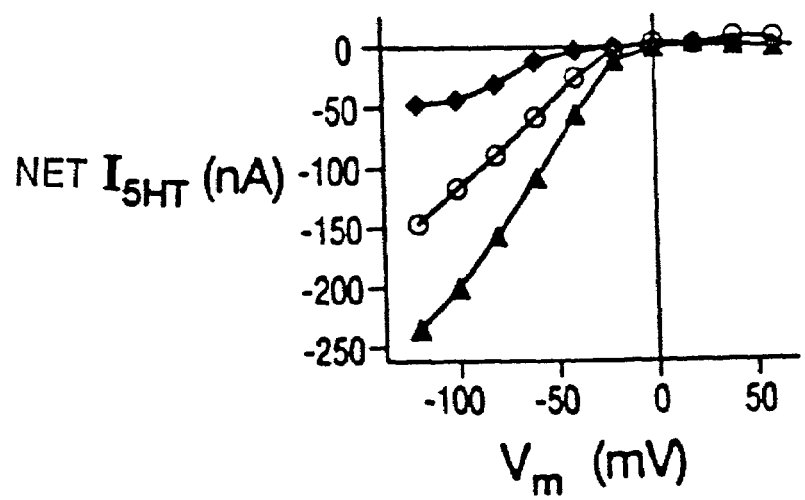
Figure 2D:
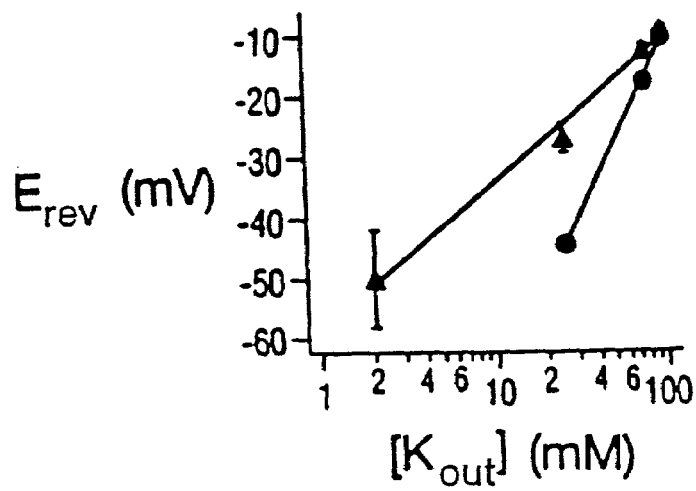

The current-voltage (I–V) characteristic of the oocyte membrane was studied by applying voltage steps from a holding potential of –80 mV. In normal ND96, in the range –140—–20 mV, only voltage- and time-independent "leak" currents were observed (FIG. 2a), and the I–V curve was linear (FIG. 2B). Above –20 mV, a slowly developing outward current was observed (FIG. 2A, a–c); this is known to be due to opening of a Cl$^-$ channel activated by Ca$^{2+}$ entry through voltage-dependent Ca$^{2+}$ channels (Barish (1983) *J. Physiol.* 342:309–325). The Ca$^{2+}$-activated Cl$^-$ current was also seen in the hK solution; in addition, the total membrane current evoked by steps to –120 and up to –20 mV was larger than in ND96 (FIGS. 2Ab; 2B), whereas above 0 mV there was little or no change. This suggested that most or all of $I_{hK}$ elicited at –80 mV by the exchange of ND96 to hK solution was due to a K$^+$ current flowing through a constitutively active inward rectifier K$^+$ channel(s). This current showed some time-dependent inactivation at –140 mV (FIG. 2Ab) and at more negative potentials; this inactivation phenomenon was not studied further. In the presence of 5HT, the membrane currents between –140 and –20 mV were further increased (FIG. 2Ac). Net 5HT-evoked currents, obtained by digital subtraction of total membrane currents in the absence of 5HT from currents in its presence (FIG. 2Ad), showed clear inward rectification; the 5HT-activated channels conducted little or no current above $E_K$ at different external K$^+$ concentrations, [K$_{out}$] (FIG. 2C). The extrapolated reversal potential of $I_{5HT}$ showed an almost perfect selectivity of the 5HT-activated channel to K$^+$, changing by about 58 mV per 10-fold change in [K$_{out}$] (FIG. 2D). The reversal potential of the total membrane current in the absence of 5HT also depended on [K$_{out}$] (FIG. 2B) but changed only by 24 mV per tenfold change in [K$_{out}$] (FIG. 2D). This does not necessarily imply poor ion selectivity of the constitutively active inward rectifier, but may reflect the relatively high contribution of Cl$^-$ and Na$^+$ to the resting membrane conductance (Dascal et al. (1984) *J. Physiol.* 352:.551–574).

Figure 3D:
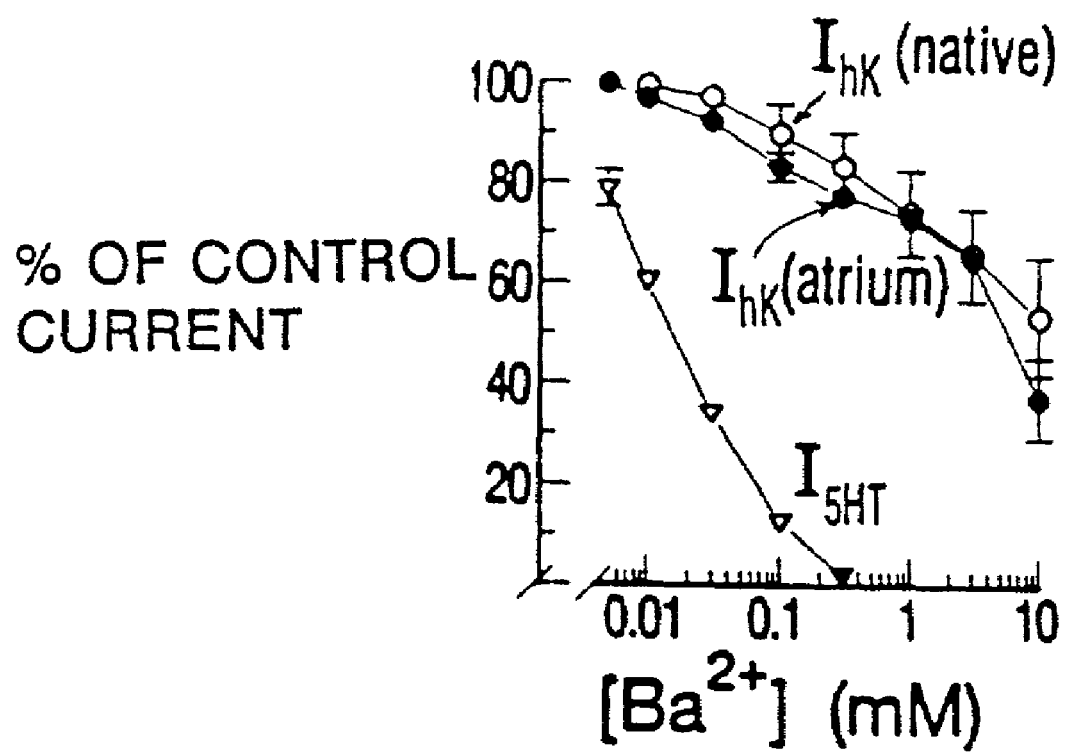

Block by external Ba$^{2+}$ is one of the characteristic features of inward rectifiers (Hille, supra.). In normal ND96 solution, Ba$^{2+}$ (5 µM-3 mM) did not cause any significant changes in resting current or conductance in native or RNA-injected oocytes at the holding potential of –80 mV. In the hK solution, Ba$^{2+}$ inhibited both $I_{hK}$ and $I_{5HT}$ (FIG. 3), and this was accompanied by a decrease in membrane conductance. 300 µM, Ba$^{2+}$ blocked about 20% of $I_{hK}$ but almost completely abolished $I_{5HT}$ (FIG. 3B). The IC$_{50}$ (half-inhibition concentration) for Ba$^{2+}$ block of $I_{5HT}$ was about 15 µM, whereas IC$_{50}$ for $I_{hK}$ block was above 3 mM (FIG. 3D). It is noteworthy that, although the sensitivity of $I_{hK}$ to Ba$^{2+}$ block was similar in native and RNA-injected oocytes, the latter did appear to have a small component of $I_{hK}$ inhibited by low doses of Ba$^{2+}$ (FIG. 3D). This raises the possibility that the atrial $I_{hK}$ is more sensitive to Ba$^{2+}$ block than the oocyte's $I_{hK}$, or that a fraction of the highly Ba$^{2+}$-sensitive channels underlying $I_{5HT}$ could be active in the absence of agonist. Note also that there was an inward current "tail" observed when Ba$^{2+}$ and 5HT was washed out simultaneously (FIG. 3B), presumably because the rate-limiting step in deactivation of the channel proceeds more slowly than unblock from Ba$^{2+}$.

To estimate the size of RNA encoding the expressed inward rectifiers, ventricle poly(A) RNA was fractionated on a sucrose gradient. The size distribution of the fractions was measured by RNA gel blots probed with [$^{32}$P] -labeled poly(T) (Lubbert et al. (1987) *J. Neurosci.* 7:1159–1165). The RNA encoding $I_{5HT}$ was found mainly in two size fractions covering the range between 2.5 and 5.5 kb. The peak expression of ventricle $I_{hK}$ was in lower size fractions, in the 1.5–3 kb range.

Figure 4A:
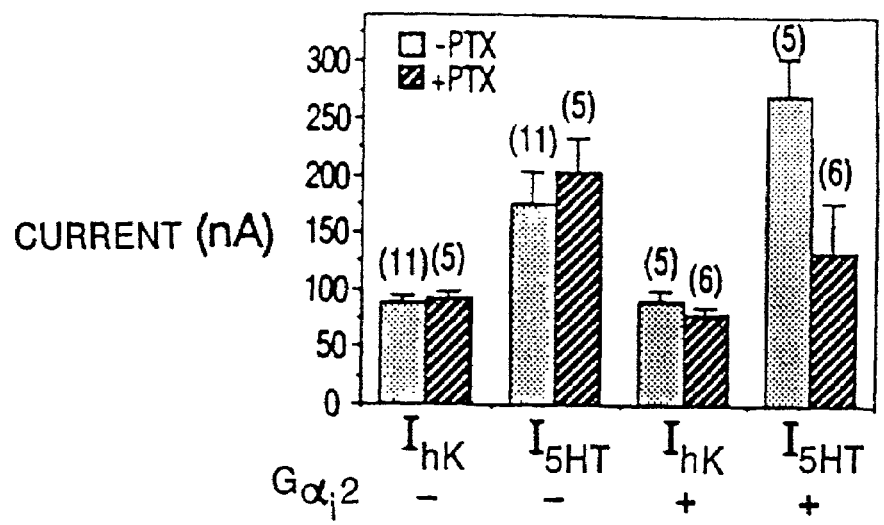
FIGS. 4A–B depict that $I_{5HT}$ is mediated by activation of a G-protein. (A) The effect of PTX treatment (500 ng/ml, 20–26 h) on $I_{hk}$ and $I_{5HT}$. The cells were injected with 120 ng/oocyte total atrial RNA, 11 ng/oocyte 5HT1A-R RNA, and, where indicated, with 11 ng/oocyte $G_{i2}$* RNA. (B) GDP-*-S injection inhibits $I_{5HT}$ but not $I_{hk}$ in an oocyte injected with atrial+5HT1A-R RNAs. 5HT concentration was 0.4 *M. A small outward current deflection (denoted by ★) upon washout of 5HT was caused by an inadvertent perfusion of ND96 for a few seconds.
Figure 4B:
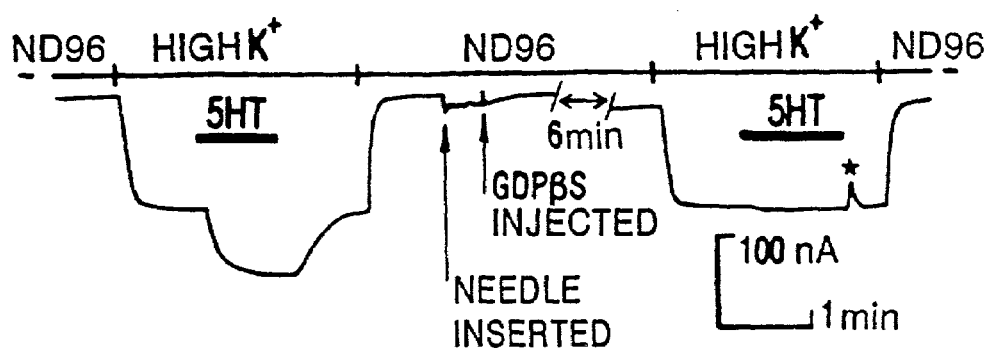

In atrium, the muscarinic receptor is coupled to the KG channel via a PTX-sensitive G-protein. Surprisingly, in RNA-injected oocytes, $I_{5HT}$ was not affected by treatment with PTX; neither was $I_{hK}$ (FIG. 4A). To test whether the 5HT1A receptor couples to the K$^+$ channel via a G-protein, the oocytes were injected with 400–800 pmole/oocyte of the non-hydrolysable analog of GDP, GDP-β-S, which is known to inhibit the activity of PTX-sensitive as well as of PTX-insensitive G-proteins (Gilman (1987) *A. Rev. Biochem.* 56:615–649). In 4 cells, GDP-β-S injection had no effect on $I_{hK}$ (115±8% of control) but strongly inhibited $I_{5HT}$, to 4±1% of control (FIG. 4B). Thus, it appears that the coupling between the 5HT1A receptor and the KG channel occurs via an oocyte's endogenous PTX-insensitive G-protein.

We examined whether an overexpressed PTX-sensitive α subunit of a G-protein, e.g. G$_{i2}$α, could compete with the "native" PTX-insensitive α subunit for the expressed 5HT1A receptor, thus restoring the PTX sensitivity of the KG channel activation. As shown in FIG. 4A, in oocytes injected with atrial RNA plus cRNAs encoding 5HT1A-R and G$_{i2}$α, PTX inhibited $I_{5HT}$ by about 50% (P<0.01, two-tailed t-test), whereas $I_{hK}$ was unaffected.

DISCUSSION

The present results demonstrate for the first time that the atrial inward rectifier K$^+$ (KG) channel, which in the native tissue is activated by ACh via a PTX-sensitive G-protein, is expressed in oocytes injected with atrial RNA. Current through the channel can be activated by acetylcholine (ACh) or, if RNA encoding a neuronal 5HT1A receptor in co-injected with atrial RNA, by serotonin (5HT). Activation of the channel probably occurs via a muscarinic ACh receptor synthesized following atrial RNA injection, rather than via the oocyte's endogenous muscarinic receptor. The latter couples to phospholipase C, and its activation induces very characteristic large transient Cl⁻ current responses caused by $Ca^{2+}$ release from intracellular stores (Dascal (1987) *CRC Crit. Rev. Biochem.* 22:317–387). Fortunately, the majority of oocyte batches lose this response after defolliculation (Miledi & Woodward (1989) *J. Physiol.* 416:601–621), and this response was not observed in the present study. Because the ACh-evoked currents were small in most cases, we concentrated on the study of the 5HT response; the latter was undoubtedly mediated by the introduced 5HT1A receptor, as 5HT was ineffective in oocytes not injected with 5HT1A-RNA, and the response displayed the expected pharmacological properties.

The evidence presented here indicates that, in oocytes injected with atrial and 5HT1A-R RNAs, activation of the 5HT1A receptor leads to opening of a K⁺ channel that bears distinctive features of an inward rectifier, similar to those of the atrial KG: i) it conducts inward but not outward K⁺ current; ii) it is blocked by low concentrations of $Ba^{2+}$, iii) the conductance of the channel does not depend solely on voltage but on ($E-E_K$). The expression of this channel must truly be directed by atrial RNA, because: i) no hormone or transmitter-activated current of this kind is observed in native oocytes; ii) expression of 5HT1A receptor alone does not cause the appearance of such a response. Based on ventricle RNA fractionation data, the RNA encoding the 5HT-activated channel is in a broad size range between 2.5 and 5.5 kb. This is similar or somewhat smaller than the reported 4–5 kb mRNA size of some constitutively active inward rectifiers expressed in Xenopus oocytes (Lewis et al. (1991) *FEBS Lett.* 290:17–21; and Perier et al. (1992) *J. Neurochem.* 59:1971–1974), as well as of the cloned IRK1 (5.5 kb) and ROMK1 (4 kb) channels. The properties of $I_{5HT}$ directed by ventricle and atrial RNA are very similar, and it is reasonable to assume that they are encoded by the same RNA species.

Opening of the inward rectifier by 5HT is mediated by activation of a G-protein, as expected for the KG channel, because i) 5HT1A receptor belongs to the family of 7-helix receptors all of which act via G-proteins (Dascal (1987) supra.); ii) $I_{5HT}$ was inhibited by intracellular injection of GDP-β-S. However, the G-protein participating in this pathway was PTX-insensitive, possibly an endogenous oocyte G-protein. It is not clear why in the oocyte the channel activation pathway involves a PTX-insensitive G-protein. The atrial KG channel normally couples to $G_i$ (Brown & Birnbaumer, supra.), and there are at least two subspecies of $G_i$ in the oocyte (Olate et al. (1990) *FEBS Lett.* 268:27–31); also, some $G_i$ may be expressed from atrial RNA. Also, in the hippocampus, the 5HT1A receptor opens a K⁺ channel by activating a PTX-sensitive G-protein. One possibility is that a vast excess of this undefined PTX-insensitive G-protein overrides the others in competition for coupling to the 5HT1A receptor. Whatever the reason for this unexpected coupling, our results show that the PTX sensitivity of the KG channel activation can be partially restored by overexpression of the α subunit of $G_i$. Since the actual identify of the α subunit does not seem to be important for activation of the expressed KG channel, these results imply that the βγ subunit complex doublet may be the activator of the channel in this case.

Atrial and ventricle RNAs also induce an enhanced activity of an additional inward rectifier, that is active in the absence of any specific stimulation (referred to as $I_{hK}$ herein). $I_{hK}$ in atrial RNA-injected oocytes is about twice as large as in native oocytes or oocytes injected with 5HT1A-R RNA alone. This current does not appear to represent the "basal" activity of the same channel activated by 5HT or ACh because it has a much lower sensitivity to $Ba^{2+}$ block. Moreover, the fractionation data indicates that the RNA directing the expression of $I_{hK}$ is smaller than that encoding the KG channel. However, it is not clear whether this atrial (or ventricle) RNA encodes the channel itself or a factor that enhances the expression or the activity of a native channel. Further studies, such as expression cloning, will help to identify the messages encoding the two inward rectifiers whose expression is reported here.

EXAMPLE 2

Formation of Heteromultimeric Kir3.0 Channels

Materials and Methods

Plasmids and DNAS. To isolate Kir3.2 and Kir3.3 from mouse brain RNA, oligonucleotides were designed that anneal to the first assigned methionine codon and the assigned stop codon of mouse Kir3.2 and Kir3.3 (Lesage et al (1994) *FEBS Lett.* 353:37–42). Kir3.0-specific sequences were coupled to a 5'-end untranslated sequence from alfalfa mosaic virus (Jobling and Gehrke (1987) *Nature* 325:622–625) and a T7 RNA polymerase recognition site to confer an optimal translational initiation site and allow RNA synthesis in vivo (cRNA). At the 3' end, a poly(A) tail was added to confer RNA stability. Total RNA from adult mouse brain (purchased from Clontech) was used as template for cDNA synthesis (Sambrook et al., supra.). PCR was conducted in a thermal cycler (Perkin-Elmer) by using Vent Polymerase (New England Biolabs), which minimizes misincorporations during the amplification step. Kir3.2 and Kir3.3 PCR-derived sequences were then inserted into the pNoTA vector (5 Prime→3 Primer, Inc.) for subsequent sequence analysis.

Kir3.1 cloned from cardiac atrium and inserted originally in pBluescript (Stratagene) was transferred to the vector pMXT (gift from J. Yang; University of Texas, Dallas), in which the cloning site is flanked by 5' and 3' untranslated sequences from Xenopus globin. G protein subunits $G_{\beta 1}$ and $G_{\gamma 2}$ cDNAs were in the pFrogy vector (gift from L. Jan, University of California, San Francisco), as described in Lim et al. (1995) *J. Gen. Physiol.* 105:421–439. The m2R cDNA (gift from E. Peralta, Harvard University) was in the pGEM3 vector (Promega).

RNA Synthesis and Oocyte Injections. Kir3.2 and Kir3.3 cRNAs were synthesized directly from gel-isolated PCR products, while the remaining cRNAs were synthesized from linearized plasmid DNAs. cRNAs were dissolved in sterile water and injected into state V or VI Xenopus oocytes as described in Quick and Lester (1994) in *Ion Channels of Excitable Cells*, ed. Narahashi (Academic, San Diego) pp.261–279. Oocytes were maintained in ND96 solution. Oocytes were assayed 2–5 days after injection.

Electrophysiology. Whole-cell currents from oocytes were measured by using an Axoclamp 2A or Geneclamp 500 amplifier (Axon Instruments, Foster City, Calif.) in the two-electrode, voltage-clamp configuration. Current and voltage electrodes were filled with 3 M KCl to yield resistances ranging from 0.5 to 1.5 MΩ. Recordings were started in an external solution (0 K⁺) containing 98 mM NaCl, 1 mM $MgCl_2$, and 5 mM Hepes, pH 7.3. In high-K⁺-containing solutions, the NaCl was replaced either completely by 98 mM KCl (98 K⁺), or partially, by 20 mM KCl (20 K⁺).

Cell-attached recordings of single channels were recorded from Xenopus oocytes as described in Methfessel et al. (1986) Pflugers Arch. 407, 577–588. Pipette solutions contained 150 mM KCl, 1 mM $CaCl_2$, and 5 mM Hepes, pH 7.3 with KOH. Bath solution contained 150 mM KCl, 1 mM $MgCl_2$, 1 mM EGTA, and 5 mM Hepes, pH 7.3 with KOH. For single-channel analysis, the current traces were filtered at 2 kHz and sampled at 10 kHz. Current amplitude histograms and open-time durations were obtained by using FETCHAN and pSTAT from pCLAMP 6.0 (Axon Instruments). All recordings were performed at room temperature ($\approx 22°$ C.).

Results

Kir3.1 is abundantly expressed in cardiac atrium and brain. When heterologously expressed in Xenopus oocytes, Kir3.1 induces strong inwardly rectifying $K^+$ currents either with m2R activation or with coexpression of G-protein subunits $G_{\beta 1}$ and $G_{\gamma 2}$.

Because expression of Kir3.2 and Kir3.1 was consistently smaller than for other channels expressed in oocytes, the effects of Kir3.1 and Kir3.2 coexpression under conditions of maximal m2R activation [1 µM acetylcholine (ACh)] were examined. With the coinjection of Kir3.1 and Kir3.2 (Kir3.1+2) cRNAs (0.5 ng each per oocyte), exposure to ACh in these oocytes led to development of large inward currents when the voltage was jumped from 0 mV to more negative values. By contrast, in oocytes injected with Kir3.2 or Kir3.1 cRNAs (1 ng), receptor activated currents were much smaller in amplitude, comparable to levels reported previously. On average, Kir3.1+2 currents [inward currents induced by ACh ($I_{K,ACh}$)=−6.4±0.8 µA; mean±SEM; n=5] were about 9-fold larger than Kir3.2 currents ($I_{K,ACh}$=−698±98 nA; n=7) and 17-fold larger than Kir3.1 currents ($I_{K,ACh}$=−365±45 nA; n=5).

Kir3.1 expressed in oocytes shows distinctive gating kinetics, including slow phases of activation (several hundred ms) during a jump from 0 mV to more negative potentials. For a similar voltage jump, Kir3.2 expressed in oocytes showed kinetics that more closely resemble other strong inward rectifiers, with a prominent phase of inactivation. These differences may be governed at least partially by differences in the sequence of the P region. The coexpressed subunits showed a slow phase of activation, but the time course of this activation cannot be explained as a simple weighted sum of the waveforms for Kir3.1 alone and Kir3.2 alone. Thus, the relations for jumps to voltages between −60 and −140 mV were well described by two exponential components with nearly voltage-independent time constants; at −80 mV the time constant of the slower component was 213±12 ms (n=4), or less than half that for Kir3.1 (32). These kinetic differences indicate molecular interactions between the Kir3.1 and Kir3.2 channels.

The large enhancement of the agonist-evoked currents for coexpressed channels might be explained by effects on any component in the receptor-channel signaling pathway, including receptors, endogenous G proteins, or the channels themselves. To discriminate among these possibilities, the receptor was uncoupled from the channel by overexpression of G protein subunits Gβ1 and $G_{\gamma 2}$. Importantly, cells expressing Gβ1γ2 and Kir3.2 showed persistent inwardly rectifying currents at amplitudes comparable or larger to those observed for m2R activation of Kir3.2. Therefore, Kir3.2, like Kir3.1, is activated by Gβγ.

Cells coexpressing Kir3.2 and Kir3.1 (Kir3.1+2) responded to high-$K^+$ solution with much larger currents than did cells expressing only Kir3.1 or Kir3.2, consistent with the results obtained with m2R activation. On average, Kir3.1+2 currents ($I_K$=−4.3±1 µA; n=7) were 14 times larger than Kir3.2 currents ($I_K$=−305±56 nA; n=7) and 40 times larger than Kir3.1 currents ($I_K$=−104±10 nA; n=6). Thus, these experiments demonstrate that the large mutual potentiating effect of Kir3.1+2 is independent of the method of G-protein activation and argue that the effects are on the channels themselves.

An increase in the number of channels or modification of the intrinsic channel properties might account for this potentiation. Single-channel recordings of Kir3.1+2 in combination or of Kir3.2 alone were made to test these possibilities. In oocytes coinjected with cRNAs for Kir3.2, Gβ1, and Gγ2, single-channel currents in the cell-attached configuration displayed features consistent with macroscopic measurements, i.e. with hyperpolarization of the unit conductance increased. No outward currents were detected at membrane potentials positive to the $K^+$equilibrium potential ($E_K$; $\approx 0$ mV). These channels openings had a mean slope conductance of 30±2pS (n=4) over the range from −40 to −100 mV, significantly smaller than the value of 39 pS for Kir3.1 alone, and showed bursts of flicker activity. Mean open-time distribution could be described by a fast component of 0.1 ms (35% of the total number of events) and a main slower component of 0.5 ms (65% of the total number of events).

The combination of Kir3.1+2 produced unitary currents with strong inward rectification and a mean slope conductance of 35±3 pS (n=4), intermediate between the values for Kir3.1 alone and Kir3.2 alone. In addition, Kir3.1+2 channels displayed markedly longer openings than Kir3.2 channels. Recordings from Kir3.1+2 channels showed a 7-fold increase in the major component of open-time duration (3.5 ms; 71% of the total number of events; there was also a smaller component of 0.5 ms; 29% of the total number of events) compared to Kir3.2. Qualitatively, the Kir3.1+2 patch recordings are rather similar to those observed for Kir3.1 in terms of mean open time, although the typically low expression levels for Kir3.1 alone vitiate systematic comparisons. At present, it is not known whether this increase, like the increase in macroscopic currents on Kir3.1+2 coexpression, is solely explained by the increase in open-time duration or whether the enhanced currents also arise from an increase in the number of openings, either because each channel opens more often or because there are more functional channels.

The effects of Kir3.3 coexpression was tested with Kir3.1 or Kir3.2. Injection of Kir3.3, $G\beta_1$, and Gγ2 cRNAs did not activate inward currents in high-$K^+$-containing solution; nor were currents activated by opioid receptors. Nevertheless, Kir3.3 had profound effects when coexpressed with Kir3.1. Coexpression of Kir3.1 and Kir3.3 (Kir3.1+3) resulted in 7-fold larger $I_K$ currents ($I_K$=−3.4±0.5 µA; n=6) than for Kir3.1 alone ($I_K$=−481±43 nA; n=6). Such augmentation was seen for each of several batches of oocytes and cRNAs and on activation of the m2R pathway. Thus, these results demonstrate that Kir3.3, despite not being directly activated by G protein subunits $G\beta_1$ and $G\gamma_2$, can interact with, and increase, G-protein-mediated responses of Kir3.1.

Surprisingly, Kir3.3 had a suppressing effect when coexpressed with Kir3.2. Gβγ-induced, inwardly rectifying currents in oocytes coinjected with Kir3.2 and Kir3.3 cRNAs (0.5 ng each per oocyte) ($I_K$=−129±22 nA; n=7) were much smaller than in oocytes injected with Kir3.2 cRNA alone (1 ng per oocyte) $I_K$=−5.1±0.6 µA; n=9). This dominant-negative effect of GlRk3 on Kir3.2 currents was also observed when m2R was coexpressed, instead of G-protein subunits $G\beta_1$ and $G\gamma_2$.

A very important issue is raised by the occurrence of heteromultimeric channels is their differential distribution in excitable tissues and their physiological significance. Distinct Kir3.0 heteromultimeric channels may be modulated or activated by G proteins differentially, as reported for other G protein effectors. This allows for a larger degree of flexibility in the control of this important form of neuronal signaling.

The plasmid pBSIIKS(−)KGA, encoding the rat inward rectifier, G-protein activated, mammalian, potassium KGA channel was deposited on May 17, 1993 with the American Type Culture Collection (ATCC), 12301 Parklawn Drive, Rockville, Md. 20852, U.S.A., under the provisions of the Budapest Treaty for the International Recognition of the Deposition of Microorganism for the Purposes of Patent Procedure, and given the ATCC accession number 75469.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for screening for agents that inhibit the activity of a Kir3.0 channel, the method comprising:
   a) combining at least two different inward rectifier, G-protein activated, mammalian, potassium Kir3.0 polypeptides in a cell to form a functional Kir3.0 channel;
   b) combining the candidate agent with said Kir3.0 channel under conditions that permit inward K+current;
   c) determining the induced current, wherein a reduction in said induced current in the presence of said agent as compared to a control is indicative that said agent inhibits the activity of a Kir3.0 channel,
   wherein at least one of said Kir3.0 polypeptides are selected from the group consisting of polypeptides having at least about 90% amino acid sequence identity with a Kir3.1 polypeptide encoded by the nucleic acid of SEQ ID NO: 7, a Kir3.2 polypeptide encoded by the nucleic acid of SEQ ID NO:11, a Kir3.3 polypeptide encoded by the nucleic acid of SEQ ID NO:12, and a Kir3.4 polypeptide encoded by the nucleic acid of SEQ ID NO:16.

2. A method for screening for agents that inhibit the activity of a Kir3.0 channel, the method comprising:
   a) providing a functional Kir3.0 channel formed by introducing into an expression host cell a nucleic acid encoding a first mammalian Kir3.0 polypeptide and a nucleic acid encoding a second mammalian Kir3.0 polypeptide under conditions that permit expression of said nucleic acid, wherein said first and second mammalian Kir3.0 polypeptides are different from each other, wherein said mammalian Kir3.0 polypeptides assemble to form a functional Kir3.0 in said expression host cell;
   b) combining a candidate agent with a functional Kir3.0 channel under conditions that permit inward K+current;
   c) determining the induced current, wherein a decrease in said induced current in the presence of said agent as compared to a control is indicative that said agent inhibits the activity of a Kir3.0 channel,
   wherein at least one of said Kir3.0 polypeptides are selected from the group consisting of polypeptides having at least about 90% amino acid sequence identity with a Kir3.1 polypeptide encoded by the nucleic acid of SEQ ID NO: 7, a Kir3.2 polypeptide encoded by the nucleic acid of SEQ ID NO:11, a Kir3.3 polypeptide encoded by the nucleic acid of SEQ ID NO:12, and a Kir3.4 polypeptide encoded by the nucleic acid of SEQ ID NO:16.

3. A screening assay for identifying materials which inhibit the activity of a Kir3.0 channel, comprising the steps of:
   (a) introducing nucleic acid encoding a Kir3.0 channel formed from at least two different inward rectifier, G-protein activated, mammalian, potassium Kir3.0 polypeptides into an expression system and causing the expression system to express said nucleic acid encoding a Kir3.0 channel;

(b) contacting the Kir3.0 channel with one or more candidate channel-inhibiting materials;

(c) selecting candidate material(s) which inhibit said activity relative to a control performed in their absence, wherein at least one of said Kir3.0 polypeptides are selected from the group consisting of polypeptides having at least about 90% amino acid sequence identity with a Kir3.1 polypeptide encoded by the nucleic acid of SEQ ID NO: 7, a Kir3.2 polypeptide encoded by the nucleic acid of SEQ ID NO:11, a Kir3.3 polypeptide encoded by the nucleic acid of SEQ ID NO:12, and a Kir3.4 polypeptide encoded by the nucleic acid of SEQ ID NO:16.

* * * * *

SEQUENCE LISTING

```
<160> NUMBER OF SEQ ID NOS: 16

<210> SEQ ID NO 1
<211> LENGTH: 2070
<212> TYPE: DNA
<213> ORGANISM: Rattus norvegicus
<220> FEATURE:
<221> NAME/KEY: CDS
<222> LOCATION: (32)..(1534)

<400> SEQUENCE: 1
ggcacgagaa tctggatctc ccctccgtat t atg tct gca ctc cga agg aaa         52
                                   Met Ser Ala Leu Arg Arg Lys
                                    1               5 ttt ggg gac gat tac cag gta gtg acc act tcg tcc agc ggt tcg ggc       100
Phe Gly Asp Asp Tyr Gln Val Val Thr Thr Ser Ser Ser Gly Ser Gly
             10                  15                  20 ttg cag ccc cag ggg cca gga cag ggc cca cag cag cag ctt gta ccc       148
Leu Gln Pro Gln Gly Pro Gly Gln Gly Pro Gln Gln Gln Leu Val Pro
         25                  30                  35 aag aag aaa cgg cag cgg ttc gtg gac aag aac ggt cgg tgc aat gtg       196
Lys Lys Lys Arg Gln Arg Phe Val Asp Lys Asn Gly Arg Cys Asn Val
 40                  45                  50                  55 cag cac ggc aac ctg ggc agc gag acc agt cgc tac ctt tcc gac ctc       244
Gln His Gly Asn Leu Gly Ser Glu Thr Ser Arg Tyr Leu Ser Asp Leu
                 60                  65                  70 ttc acc acc ctg gtg gat ctc aag tgg cgt tgg aac ctc ttt atc ttc       292
Phe Thr Thr Leu Val Asp Leu Lys Trp Arg Trp Asn Leu Phe Ile Phe
             75                  80                  85 atc ctc acc tac acc gtg gcc tgg ctc ttc atg gcg tcc atg tgg tgg       340
Ile Leu Thr Tyr Thr Val Ala Trp Leu Phe Met Ala Ser Met Trp Trp
         90                  95                 100 gtg atc gct tat acc cgg ggc gac ctg aac aaa gcc cat gtc ggc aac       388
Val Ile Ala Tyr Thr Arg Gly Asp Leu Asn Lys Ala His Val Gly Asn
    105                 110                 115 tac act ccc tgt gtg gcc aat gtc tat aac ttc ccc tct gcc ttc ctt       436
Tyr Thr Pro Cys Val Ala Asn Val Tyr Asn Phe Pro Ser Ala Phe Leu
120                 125                 130                 135 ttc ttc atc gag acc gag gcc acc atc ggc tat ggc tac cgc tac atc       484
Phe Phe Ile Glu Thr Glu Ala Thr Ile Gly Tyr Gly Tyr Arg Tyr Ile
                140                 145                 150 acc gac aag tgc ccc gag ggc atc atc ctt ttc ctt ttc cag tcc atc       532
Thr Asp Lys Cys Pro Glu Gly Ile Ile Leu Phe Leu Phe Gln Ser Ile
            155                 160                 165 ctt ggc tcc atc gtg gac gct ttc ctc atc ggc tgc atg ttc atc aag       580
Leu Gly Ser Ile Val Asp Ala Phe Leu Ile Gly Cys Met Phe Ile Lys
        170                 175                 180
```

-continued

| | | |
|---|---|---|
| atg tcc cag ccc aaa aag cgc gcc gag acc ctc atg ttt agc gag cat<br>Met Ser Gln Pro Lys Lys Arg Ala Glu Thr Leu Met Phe Ser Glu His<br>185                       190                     195 | 628 |
| gcg gtt att tcc atg agg gac gga aaa ctc act ctc atg ttc cgg gtg<br>Ala Val Ile Ser Met Arg Asp Gly Lys Leu Thr Leu Met Phe Arg Val<br>200                       205                    210                 215 | 676 |
| ggc aac ctg cgc aac agc cac atg gtc tcc gcg cag atc cgc tgc aag<br>Gly Asn Leu Arg Asn Ser His Met Val Ser Ala Gln Ile Arg Cys Lys<br>                    220                    225                  230 | 724 |
| ctg ctc aaa tct cgg cag aca cct gag ggt gag ttt cta ccc ctt gac<br>Leu Leu Lys Ser Arg Gln Thr Pro Glu Gly Glu Phe Leu Pro Leu Asp<br>          235                    240                    245 | 772 |
| caa ctt gaa ctg gat gta ggt ttt agt aca ggg gca gat caa ctt ttt<br>Gln Leu Glu Leu Asp Val Gly Phe Ser Thr Gly Ala Asp Gln Leu Phe<br>          250                    255                    260 | 820 |
| ctt gtg tcc cct ctc acc att tgc cac gtg atc gat gcc aaa agc ccc<br>Leu Val Ser Pro Leu Thr Ile Cys His Val Ile Asp Ala Lys Ser Pro<br>265                       270                    275 | 868 |
| ttt tat gac cta tcc cag cga agc atg caa act gaa cag ttc gag gtg<br>Phe Tyr Asp Leu Ser Gln Arg Ser Met Gln Thr Glu Gln Phe Glu Val<br>280                       285                    290                 295 | 916 |
| gtc gtc atc ctg gaa ggc atc gtg gaa acc aca ggg atg act tgt caa<br>Val Val Ile Leu Glu Gly Ile Val Glu Thr Thr Gly Met Thr Cys Gln<br>                    300                    305                  310 | 964 |
| gct cga aca tca tac acc gaa gat gaa gtt ctt tgg ggt cat cgt ttt<br>Ala Arg Thr Ser Tyr Thr Glu Asp Glu Val Leu Trp Gly His Arg Phe<br>          315                    320                    325 | 1012 |
| ttc cct gta att tct tta gaa gaa gga ttc ttt aaa gtc gat tac tcc<br>Phe Pro Val Ile Ser Leu Glu Glu Gly Phe Phe Lys Val Asp Tyr Ser<br>          330                    335                    340 | 1060 |
| cag ttc cat gca acc ttt gaa gtc ccc acc cct ccg tac agt gtg aaa<br>Gln Phe His Ala Thr Phe Glu Val Pro Thr Pro Pro Tyr Ser Val Lys<br>345                       350                    355 | 1108 |
| gag cag gaa gaa atg ctt ctc atg tct tcc cct tta ata gca cca gcc<br>Glu Gln Glu Glu Met Leu Leu Met Ser Ser Pro Leu Ile Ala Pro Ala<br>360                       365                    370                 375 | 1156 |
| ata acc aac agc aaa gaa aga cac aat tct gtg gag tgc tta gat gga<br>Ile Thr Asn Ser Lys Glu Arg His Asn Ser Val Glu Cys Leu Asp Gly<br>                    380                    385                  390 | 1204 |
| cta gat gac att agc aca aaa ctt cca tcg aag ctg cag aaa att acg<br>Leu Asp Asp Ile Ser Thr Lys Leu Pro Ser Lys Leu Gln Lys Ile Thr<br>                    395                    400                  405 | 1252 |
| ggg aga gaa gac ttt ccc aaa aaa ctc ctg agg atg agt tct aca act<br>Gly Arg Glu Asp Phe Pro Lys Lys Leu Leu Arg Met Ser Ser Thr Thr<br>          410                    415                    420 | 1300 |
| tca gaa aaa gcc tat agt ttg ggt gat ttg ccc atg aaa ctc caa cga<br>Ser Glu Lys Ala Tyr Ser Leu Gly Asp Leu Pro Met Lys Leu Gln Arg<br>425                       430                    435 | 1348 |
| ata agt tcg gtt cct ggc aac tct gaa gaa aaa ctg gta tct aaa acc<br>Ile Ser Ser Val Pro Gly Asn Ser Glu Glu Lys Leu Val Ser Lys Thr<br>440                       445                    450                 455 | 1396 |
| acc aag atg tta tca gat ccc atg agc cag tct gtg gcc gat ttg cca<br>Thr Lys Met Leu Ser Asp Pro Met Ser Gln Ser Val Ala Asp Leu Pro<br>                    460                    465                  470 | 1444 |
| ccg aag ctt caa aag atg gct gga gga cct acc agg atg gaa ggg aat<br>Pro Lys Leu Gln Lys Met Ala Gly Gly Pro Thr Arg Met Glu Gly Asn<br>          475                    480                  485 | 1492 |
| ctt cca gcc aaa cta aga aaa atg aac tct gac cgc ttc aca<br>Leu Pro Ala Lys Leu Arg Lys Met Asn Ser Asp Arg Phe Thr | 1534 |

-continued

```
                 490         495         500
tagcaaaaca ccccattagg cattatttca tgttttgatt tagttttagt ccaatatttg    1594
gctgataaga taatcctccc cgggaaatct gagaggtcta tcccagtctg gcaaattcat    1654
cagaggactc ttcattgaag tgttgttact gtgttgaaca tgagttacaa agggaggaca    1714
tcataagaaa gctaatagtt ggcatgtatt atcacatcaa gcatgcaata atgtgcaaat    1774
tttgcattta gttttctggc atgatttata tatggcatat ttatattgaa tattctggaa    1834
aaatatataa atatatattt gaagtggaga tattctcccc ataatttcta atatatgtat    1894
taagccaaac atgagtggat agctttcagg gcactaaaat aatatacatg catacataca    1954
tacatgcata tgcacagaca catacacaca catactcata tatataaaac atacccatac    2014
aaacatatat atctaataaa aattgtgatg ttttgttcaa aaaaaaaaaa aaaaaa        2070
```

<210> SEQ ID NO 2
<211> LENGTH: 501
<212> TYPE: PRT
<213> ORGANISM: Rattus norvegicus

<400> SEQUENCE: 2

```
Met Ser Ala Leu Arg Arg Lys Phe Gly Asp Asp Tyr Gln Val Val Thr
1               5                   10                  15

Thr Ser Ser Ser Gly Ser Gly Leu Gln Pro Gln Gly Pro Gly Gln Gly
            20                  25                  30

Pro Gln Gln Gln Leu Val Pro Lys Lys Arg Gln Arg Phe Val Asp
        35                  40                  45

Lys Asn Gly Arg Cys Asn Val Gln His Gly Asn Leu Gly Ser Glu Thr
    50                  55                  60

Ser Arg Tyr Leu Ser Asp Leu Phe Thr Thr Leu Val Asp Leu Lys Trp
65                  70                  75                  80

Arg Trp Asn Leu Phe Ile Phe Ile Leu Thr Tyr Thr Val Ala Trp Leu
                85                  90                  95

Phe Met Ala Ser Met Trp Trp Val Ile Ala Tyr Thr Arg Gly Asp Leu
            100                 105                 110

Asn Lys Ala His Val Gly Asn Tyr Thr Pro Cys Val Ala Asn Val Tyr
        115                 120                 125

Asn Phe Pro Ser Ala Phe Leu Phe Phe Ile Glu Thr Glu Ala Thr Ile
    130                 135                 140

Gly Tyr Gly Tyr Arg Tyr Ile Thr Asp Lys Cys Pro Glu Gly Ile Ile
145                 150                 155                 160

Leu Phe Leu Phe Gln Ser Ile Leu Gly Ser Ile Val Asp Ala Phe Leu
                165                 170                 175

Ile Gly Cys Met Phe Ile Lys Met Ser Gln Pro Lys Lys Arg Ala Glu
            180                 185                 190

Thr Leu Met Phe Ser Glu His Ala Val Ile Ser Met Arg Asp Gly Lys
        195                 200                 205

Leu Thr Leu Met Phe Arg Val Gly Asn Leu Arg Asn Ser His Met Val
    210                 215                 220

Ser Ala Gln Ile Arg Cys Lys Leu Leu Lys Ser Arg Gln Thr Pro Glu
225                 230                 235                 240

Gly Glu Phe Leu Pro Leu Asp Gln Leu Glu Leu Asp Val Gly Phe Ser
                245                 250                 255

Thr Gly Ala Asp Gln Leu Phe Leu Val Ser Pro Leu Thr Ile Cys His
            260                 265                 270
```

```
Val Ile Asp Ala Lys Ser Pro Phe Tyr Asp Leu Ser Gln Arg Ser Met
        275                 280                 285
Gln Thr Glu Gln Phe Glu Val Val Ile Leu Glu Gly Ile Val Glu
    290                 295                 300
Thr Thr Gly Met Thr Cys Gln Ala Arg Thr Ser Tyr Thr Glu Asp Glu
305                 310                 315                 320
Val Leu Trp Gly His Arg Phe Pro Val Ile Ser Leu Glu Glu Gly
                325                 330                 335
Phe Phe Lys Val Asp Tyr Ser Gln Phe His Ala Thr Phe Glu Val Pro
                340                 345                 350
Thr Pro Pro Tyr Ser Val Lys Glu Gln Glu Met Leu Leu Met Ser
            355                 360                 365
Ser Pro Leu Ile Ala Pro Ala Ile Thr Asn Ser Lys Glu Arg His Asn
370                 375                 380
Ser Val Glu Cys Leu Asp Gly Leu Asp Asp Ile Ser Thr Lys Leu Pro
385                 390                 395                 400
Ser Lys Leu Gln Lys Ile Thr Gly Arg Glu Asp Phe Pro Lys Lys Leu
                405                 410                 415
Leu Arg Met Ser Ser Thr Thr Ser Glu Lys Ala Tyr Ser Leu Gly Asp
                420                 425                 430
Leu Pro Met Lys Leu Gln Arg Ile Ser Ser Val Pro Gly Asn Ser Glu
                435                 440                 445
Glu Lys Leu Val Ser Lys Thr Thr Lys Met Leu Ser Asp Pro Met Ser
    450                 455                 460
Gln Ser Val Ala Asp Leu Pro Pro Lys Leu Gln Lys Met Ala Gly Gly
465                 470                 475                 480
Pro Thr Arg Met Glu Gly Asn Leu Pro Ala Lys Leu Arg Lys Met Asn
                485                 490                 495
Ser Asp Arg Phe Thr
                500

<210> SEQ ID NO 3
<211> LENGTH: 1978
<212> TYPE: DNA
<213> ORGANISM: Mus musculus
<220> FEATURE:
<221> NAME/KEY: CDS
<222> LOCATION: (488)..(1729)

<400> SEQUENCE: 3
gtctccctgc aaggtctatc actttgctcc taaacgagga tttattccct ctgccactca        60
aggctgtccc ccagtttcct cgcaaccggg cttcctcctc agtccctgcc cacacgcgca      120
ctcctctgcc ccgcggtggc cccagcgccc agccctccag ccagagggag ccaggcacca      180
gacggcagca cctggctgga gaggttgggc gggccgaggg tggggatccg cgggaaccgg      240
cgagtcggag ctggagcagg agctggaccc aaccgctagc agcagaatgg agtctcctga      300
aagcctgccg gggctgatgt gaaattgggc catctgcttc cagttggtct gtttcctcct      360
tttcttgtat tttcttccct cgccattcac cgtggagtga attattgaat cttgctccgt      420
tccgagagag gcgatcagga tggagtgaac ctaccctgtc cactacaagg aaaagcacaa      480 agaagaa atg aca atg gcc aag tta act gaa tcc atg act aac gtc ttg     529
        Met Thr Met Ala Lys Leu Thr Glu Ser Met Thr Asn Val Leu
        1               5                  10 gaa ggc gat tcc atg gac cag gat gtg gaa agc cca gtg gcc att cac     577
Glu Gly Asp Ser Met Asp Gln Asp Val Glu Ser Pro Val Ala Ile His
15                  20                  25                  30
```

-continued

```
cag cca aag ttg cct aag cag gcc agg gac gac ctg ccg aga cac atc         625
Gln Pro Lys Leu Pro Lys Gln Ala Arg Asp Asp Leu Pro Arg His Ile
             35                  40                  45 agc cga gac agg acc aaa agg aaa atc cag agg tac gtg agg aag gat         673
Ser Arg Asp Arg Thr Lys Arg Lys Ile Gln Arg Tyr Val Arg Lys Asp
     50                  55                  60 ggg aag tgc aac gtt cac cac ggc aat gtg cgg gag acc tac cga tac         721
Gly Lys Cys Asn Val His His Gly Asn Val Arg Glu Thr Tyr Arg Tyr
 65                  70                  75 ctg acg gac atc ttc acc acc ctg gtg gac ctg aag tgg aga ttc aac         769
Leu Thr Asp Ile Phe Thr Thr Leu Val Asp Leu Lys Trp Arg Phe Asn
         80                  85                  90 ctg ttg atc ttt gtc atg gtc tac aca gtg acg tgg ctt ttc ttt ggg         817
Leu Leu Ile Phe Val Met Val Tyr Thr Val Thr Trp Leu Phe Phe Gly
 95                 100                 105                 110 atg atc tgg tgg ctg att gcg tac atc cgg gga gat atg gac cac ata         865
Met Ile Trp Trp Leu Ile Ala Tyr Ile Arg Gly Asp Met Asp His Ile
                115                 120                 125 gag gac ccc tcg tgg act cct tgt gtc acc aac ctc aac ggg ttt gtc         913
Glu Asp Pro Ser Trp Thr Pro Cys Val Thr Asn Leu Asn Gly Phe Val
            130                 135                 140 tct gct ttt tta ttc tcc ata gag aca gaa acc acc atc ggt tat ggc         961
Ser Ala Phe Leu Phe Ser Ile Glu Thr Glu Thr Thr Ile Gly Tyr Gly
        145                 150                 155 tac cgg gtc atc acg gac aag tgc cct gag ggg att att ctc ctc tta        1009
Tyr Arg Val Ile Thr Asp Lys Cys Pro Glu Gly Ile Ile Leu Leu Leu
    160                 165                 170 atc cag tcc gtg ttg ggg tcc att gtc aac gcc ttc atg gta gga tgt        1057
Ile Gln Ser Val Leu Gly Ser Ile Val Asn Ala Phe Met Val Gly Cys
175                 180                 185                 190 atg ttt gtg aaa ata tcc caa ccc aag aag agg gca gag acc ctg gtc        1105
Met Phe Val Lys Ile Ser Gln Pro Lys Lys Arg Ala Glu Thr Leu Val
                195                 200                 205 ttt tcc acc cac gcg gtg atc tcc atg cgg gat ggg aaa ctg tgc ttg        1153
Phe Ser Thr His Ala Val Ile Ser Met Arg Asp Gly Lys Leu Cys Leu
            210                 215                 220 atg ttc cgg gtg ggg gac ttg agg aat tct cac att gtg gag gca tcc        1201
Met Phe Arg Val Gly Asp Leu Arg Asn Ser His Ile Val Glu Ala Ser
        225                 230                 235 atc aga gcc aag ttg atc aag tcc aaa cag act tca gag ggg gag ttt        1249
Ile Arg Ala Lys Leu Ile Lys Ser Lys Gln Thr Ser Glu Gly Glu Phe
    240                 245                 250 att ccc ctc aac cag agt gat atc aac gtg ggg tac tac aca ggg gac        1297
Ile Pro Leu Asn Gln Ser Asp Ile Asn Val Gly Tyr Tyr Thr Gly Asp
255                 260                 265                 270 gac cgg ctc ttt ctg gtg tca cca ttg att att agc cat gaa att aac        1345
Asp Arg Leu Phe Leu Val Ser Pro Leu Ile Ile Ser His Glu Ile Asn
                275                 280                 285 caa cag agt ccc ttc tgg gag atc tcc aaa gcg cag ctg cct aaa gag        1393
Gln Gln Ser Pro Phe Trp Glu Ile Ser Lys Ala Gln Leu Pro Lys Glu
            290                 295                 300 gaa ctg gag att gtg gtc atc ctg gag gga atc gtg gaa gcc aca gga        1441
Glu Leu Glu Ile Val Val Ile Leu Glu Gly Ile Val Glu Ala Thr Gly
        305                 310                 315 atg acg tgc caa gcc cga agc tcc tac atc acc agt gag atc ttg tgg        1489
Met Thr Cys Gln Ala Arg Ser Ser Tyr Ile Thr Ser Glu Ile Leu Trp
    320                 325                 330 ggt tac cgg ttc aca cct gtc cta acg atg gaa gac ggg ttc tac gaa        1537
Gly Tyr Arg Phe Thr Pro Val Leu Thr Met Glu Asp Gly Phe Tyr Glu
```

-continued

```
                 335                 340                 345                 350
gtt gac tac aac agc ttc cat gag acc tat gag acc agc acc ccg tcc    1585
Val Asp Tyr Asn Ser Phe His Glu Thr Tyr Glu Thr Ser Thr Pro Ser
                355                 360                 365 ctt agt gcc aaa gag cta gcg gag ctg gct aac cgg gca gag gtg cct    1633
Leu Ser Ala Lys Glu Leu Ala Glu Leu Ala Asn Arg Ala Glu Val Pro
            370                 375                 380 ctg agt tgg tct gtg tcc agc aaa ctg aac caa cat gca gaa ttg gag    1681
Leu Ser Trp Ser Val Ser Ser Lys Leu Asn Gln His Ala Glu Leu Glu
        385                 390                 395 aca gaa gag gaa gag aag aac ccg gaa gaa ctg acg gag agg aat ggg    1729
Thr Glu Glu Glu Glu Lys Asn Pro Glu Glu Leu Thr Glu Arg Asn Gly
    400                 405                 410 tgatgctggg ctcctagtgt ggatcaagaa gtgttccttc taagctcatc ctctgacaga  1789
cattacagag aactgatata ttttcctcc ttcactgctt ggaagaattc acccagaatt   1849
cacccacccc atctggacct agtacattct gtttgggaag gtcatcatta attttactta  1909
aagtcggcgc tggagagatg acgccgcggg ctaagatggt ttattgttct tgcagacggc  1969
ctgggttca                                                          1978
```

<210> SEQ ID NO 4
<211> LENGTH: 414
<212> TYPE: PRT
<213> ORGANISM: Mus musculus

<400> SEQUENCE: 4

```
Met Thr Met Ala Lys Leu Thr Glu Ser Met Thr Asn Val Leu Glu Gly
1               5                   10                  15

Asp Ser Met Asp Gln Asp Val Glu Ser Pro Val Ala Ile His Gln Pro
            20                  25                  30

Lys Leu Pro Lys Gln Ala Arg Asp Asp Leu Pro Arg His Ile Ser Arg
        35                  40                  45

Asp Arg Thr Lys Arg Lys Ile Gln Arg Tyr Val Arg Lys Asp Gly Lys
    50                  55                  60

Cys Asn Val His His Gly Asn Val Arg Glu Thr Tyr Arg Tyr Leu Thr
65                  70                  75                  80

Asp Ile Phe Thr Thr Leu Val Asp Leu Lys Trp Arg Phe Asn Leu Leu
                85                  90                  95

Ile Phe Val Met Val Tyr Thr Val Thr Trp Leu Phe Phe Gly Met Ile
            100                 105                 110

Trp Trp Leu Ile Ala Tyr Ile Arg Gly Asp Met Asp His Ile Glu Asp
        115                 120                 125

Pro Ser Trp Thr Pro Cys Val Thr Asn Leu Asn Gly Phe Val Ser Ala
    130                 135                 140

Phe Leu Phe Ser Ile Glu Thr Glu Thr Thr Ile Gly Tyr Gly Tyr Arg
145                 150                 155                 160

Val Ile Thr Asp Lys Cys Pro Glu Gly Ile Ile Leu Leu Leu Ile Gln
                165                 170                 175

Ser Val Leu Gly Ser Ile Val Asn Ala Phe Met Val Gly Cys Met Phe
            180                 185                 190

Val Lys Ile Ser Gln Pro Lys Lys Arg Ala Glu Thr Leu Val Phe Ser
        195                 200                 205

Thr His Ala Val Ile Ser Met Arg Asp Gly Lys Leu Cys Leu Met Phe
    210                 215                 220

Arg Val Gly Asp Leu Arg Asn Ser His Ile Val Glu Ala Ser Ile Arg
```

-continued

```
            225                 230                 235                 240
Ala Lys Leu Ile Lys Ser Lys Gln Thr Ser Glu Gly Glu Phe Ile Pro
                245                 250                 255

Leu Asn Gln Ser Asp Ile Asn Val Gly Tyr Tyr Thr Gly Asp Asp Arg
            260                 265                 270

Leu Phe Leu Val Ser Pro Leu Ile Ser His Glu Ile Asn Gln Gln
        275                 280                 285

Ser Pro Phe Trp Glu Ile Ser Lys Ala Gln Leu Pro Lys Glu Glu Leu
    290                 295                 300

Glu Ile Val Val Ile Leu Glu Gly Ile Val Glu Ala Thr Gly Met Thr
305                 310                 315                 320

Cys Gln Ala Arg Ser Ser Tyr Ile Thr Ser Glu Ile Leu Trp Gly Tyr
                325                 330                 335

Arg Phe Thr Pro Val Leu Thr Met Glu Asp Gly Phe Tyr Glu Val Asp
            340                 345                 350

Tyr Asn Ser Phe His Glu Thr Tyr Glu Thr Ser Thr Pro Ser Leu Ser
        355                 360                 365

Ala Lys Glu Leu Ala Glu Leu Ala Asn Arg Ala Glu Val Pro Leu Ser
    370                 375                 380

Trp Ser Val Ser Ser Lys Leu Asn Gln His Ala Glu Leu Glu Thr Glu
385                 390                 395                 400

Glu Glu Glu Lys Asn Pro Glu Glu Leu Thr Glu Arg Asn Gly
                405                 410
```

<210> SEQ ID NO 5
<211> LENGTH: 2301
<212> TYPE: DNA
<213> ORGANISM: Mus musculus
<220> FEATURE:
<221> NAME/KEY: CDS
<222> LOCATION: (308)..(1435)

<400> SEQUENCE: 5

```
ctgagctgcc gttacattca ggagaaacag cagtgtcggc ggctcccaat ctcagaggga      60
acctaggata ctgggggaga tggtgtcagg gacatggacg ccaaccccca agggtttctg     120
ctgctggcta ctcttctctc caggctctac ttctgttcat acggtccata tctcctaggg     180
gaccctgaaa gcctaggaac cgactctggc catccatctc tccgggaaga ttataaccca     240
gagtgcttct caggggggaa gaatttgaag caaaaccaga ccccgcagga tccccgctgc     300 ggccgcc atg gcg cag gag aac gcc gct ttc tct ccc ggg tcg gag gag        349
        Met Ala Gln Glu Asn Ala Ala Phe Ser Pro Gly Ser Glu Glu
        1               5                  10 ccg cca cgc cgc cgc ggt cgc cag cgc tac gtg gag aag gac ggt cgc        397
Pro Pro Arg Arg Arg Gly Arg Gln Arg Tyr Val Glu Lys Asp Gly Arg
15                  20                  25                  30 tgt aac gtg cag cag ggc aac gtc cgc gag acc tac cgc tac ctg acc        445
Cys Asn Val Gln Gln Gly Asn Val Arg Glu Thr Tyr Arg Tyr Leu Thr
                35                  40                  45 gac ctg ttc acc acg ctg gtg gac ctg cag tgg cgc ctc aga ctg ctc        493
Asp Leu Phe Thr Thr Leu Val Asp Leu Gln Trp Arg Leu Arg Leu Leu
            50                  55                  60 ttc ttc gtg ctc gcc tac gcg ctc act tgg ctc ttc ttc ggt gtc atc        541
Phe Phe Val Leu Ala Tyr Ala Leu Thr Trp Leu Phe Phe Gly Val Ile
        65                  70                  75 tgg tgg ctc atc gcc tac gtt cgc ggc gac ctg gag cac ctg gag gac        589
Trp Trp Leu Ile Ala Tyr Gly Arg Gly Asp Leu Glu His Leu Glu Asp
    80                  85                  90
```

```
acc gcg tgg acc ccg tgc gtc aac aac ctc aac ggc ttc gtg gcc gcc      637
Thr Ala Trp Thr Pro Cys Val Asn Asn Leu Asn Gly Phe Val Ala Ala
 95                 100                 105                 110 ttc ctc ttc tcc atc gag acg gag acc acc atc ggc tat ggg cac cgc      685
Phe Leu Phe Ser Ile Glu Thr Glu Thr Thr Ile Gly Tyr Gly His Arg
                115                 120                 125 gtc atc acc gac cag tgt ccc gag ggc atc gtg ctg ctg ctg cag          733
Val Ile Thr Asp Gln Cys Pro Glu Gly Ile Val Leu Leu Leu Gln
            130                 135                 140 gct atc ctg ggc tcc atg gtg aac gct ttc atg gtg ggc tgc atg ttc      781
Ala Ile Leu Gly Ser Met Val Asn Ala Phe Met Val Gly Cys Met Phe
            145                 150                 155 gtc aag atc tcg cag ccc aac aag cgc gcc gcc act ctc gtc ttc tcc      829
Val Lys Ile Ser Gln Pro Asn Lys Arg Ala Ala Thr Leu Val Phe Ser
160                 165                 170 tcg cac gcc gtg gtg tct ctg cgc gac ggg cgc ctc tgt ctc atg ttt      877
Ser His Ala Val Val Ser Leu Arg Asp Gly Arg Leu Cys Leu Met Phe
175                 180                 185                 190 cgc gtg ggc gac ctg cga tcc tca cac atc gtc gag gcc tcc atc cga      925
Arg Val Gly Asp Leu Arg Ser Ser His Ile Val Glu Ala Ser Ile Arg
                195                 200                 205 gcc aag ctc atc cgc tcc cgt cag acg ctc gag ggc gag ttc atc cct      973
Ala Lys Leu Ile Arg Ser Arg Gln Thr Leu Glu Gly Glu Phe Ile Pro
            210                 215                 220 ttg cac cag acc gac ctc agc gtg ggc ttt gac acg ggg gac gac cgc     1021
Leu His Gln Thr Asp Leu Ser Val Gly Phe Asp Thr Gly Asp Asp Arg
            225                 230                 235 ctc ttt ctc gtc tca cct ctc gtc atc agc cac gaa atc gat gcc gcc     1069
Leu Phe Leu Val Ser Pro Leu Val Ile Ser His Glu Ile Asp Ala Ala
240                 245                 250 agc ccc ttc tgg gag gca tcg cgc cgc gcc ctc gag agg gac gac ttc     1117
Ser Pro Phe Trp Glu Ala Ser Arg Arg Ala Leu Glu Arg Asp Asp Phe
255                 260                 265                 270 gag atc gta gtc att ctc gag ggc atg gtg gag gcc acg gga atg acg     1165
Glu Ile Val Val Ile Leu Glu Gly Met Val Glu Ala Thr Gly Met Thr
                275                 280                 285 tgc caa gct cga agc tcg tac ctg gtg gat gaa gtg ttg tgg gga cac     1213
Cys Gln Ala Arg Ser Ser Tyr Leu Val Asp Glu Val Leu Trp Gly His
            290                 295                 300 cgg ttc aca tcc gtg ctc acc ctg gag gat ggt ttc tat gag gtg gac     1261
Arg Phe Thr Ser Val Leu Thr Leu Glu Asp Gly Phe Tyr Glu Val Asp
            305                 310                 315 tac gcc agc ttc cac gaa acc ttt gag gtg ccc aca ccc tcg tgc agt     1309
Tyr Ala Ser Phe His Glu Thr Phe Glu Val Pro Thr Pro Ser Cys Ser
320                 325                 330 gct cgg gaa ctg gca gaa gcc gcg gcc cgc ctt gat gcc cat ctc tac     1357
Ala Arg Glu Leu Ala Glu Ala Ala Ala Arg Leu Asp Ala His Leu Tyr
335                 340                 345                 350 tgg tcc atc ccc agc agg ctg gat gag aag gtg gag gaa gaa ggg gct     1405
Trp Ser Ile Pro Ser Arg Leu Asp Glu Lys Val Glu Glu Glu Gly Ala
                355                 360                 365 ggg gag ggg ggc agg tgc ggg aga tgg agc tgacaaggag cacaatggct       1455
Gly Glu Gly Gly Arg Cys Gly Arg Trp Ser
            370                 375 gccacccccca gagagtgagt ccaaggtgtg actggtttcc tcccaccccc tgtggcagac  1515 caggggccg gactcaggta cacagaagct gcgagtggag gtggaagaag aggaggcagg    1575
cagtgtcccg aggaacagct aaagttggga gaggcccgct gagtccagga tcgagtaggg  1635
```

-continued

```
aaggctgagg tcctggtttg aagagagagg gttgcagggc ggggtgagag aacatgtcag   1695
tctgtctgtg tttgaccttc acatcggttc atgggtggat ggatggacag aaggatgggc   1755 tcatggggt tgatcgggaa ggtggagcag atagagacag ccaatggata atcgctcagg    1815
tggtaagtgg cttggcagtc gatgatcgtc acctgcagca cacctttgtg agaaatccat   1875 ggcatcctt tcttccaga tataggtagc ctcaaaccag ggagcgtggc ttagggagca     1935
ggctgtcagg tggactacca ccccactca cctcccctca actggcctcc ctgatgtgtg    1995
acacgcctgc ctaactagag aagagagcac tgggtagagg tggacacagg tgtggctgcc   2055
ctccccagta tcactgtccc atggcgagag gtcagaaagg caaacaaaca atgggggtag   2115
atgctgagca gggaggggcc ctgaagcagg acctggggac agccaaggac aactatttg    2175 tgagagagga atgaaacctt gcaggtcctg ccacagaagc aagaagcaga ggaaaggcca   2235
tggagagact taataaaggg ttttacaagg gaaaaaaaaa aaaaaaaaaa aaaaaaaaaa   2295
aaaaaa                                                              2301
```

<210> SEQ ID NO 6
<211> LENGTH: 376
<212> TYPE: PRT
<213> ORGANISM: Mus musculus

<400> SEQUENCE: 6

```
Met Ala Gln Glu Asn Ala Ala Phe Ser Pro Gly Ser Glu Glu Pro Pro
1               5                   10                  15

Arg Arg Arg Gly Arg Gln Arg Tyr Val Glu Lys Asp Gly Arg Cys Asn
            20                  25                  30

Val Gln Gln Gly Asn Val Arg Glu Thr Tyr Arg Tyr Leu Thr Asp Leu
        35                  40                  45

Phe Thr Thr Leu Val Asp Leu Gln Trp Arg Leu Arg Leu Phe Phe
    50                  55                  60

Val Leu Ala Tyr Ala Leu Thr Trp Leu Phe Phe Gly Val Ile Trp Trp
65                  70                  75                  80

Leu Ile Ala Tyr Gly Arg Gly Asp Leu Glu His Leu Glu Asp Thr Ala
                85                  90                  95

Trp Thr Pro Cys Val Asn Asn Leu Asn Gly Phe Val Ala Ala Phe Leu
            100                 105                 110

Phe Ser Ile Glu Thr Glu Thr Thr Ile Gly Tyr Gly His Arg Val Ile
        115                 120                 125

Thr Asp Gln Cys Pro Glu Gly Ile Val Leu Leu Leu Gln Ala Ile
    130                 135                 140

Leu Gly Ser Met Val Asn Ala Phe Met Val Gly Cys Met Phe Val Lys
145                 150                 155                 160

Ile Ser Gln Pro Asn Lys Arg Ala Ala Thr Leu Val Phe Ser Ser His
                165                 170                 175

Ala Val Val Ser Leu Arg Asp Gly Arg Leu Cys Leu Met Phe Arg Val
            180                 185                 190

Gly Asp Leu Arg Ser Ser His Ile Val Glu Ala Ser Ile Arg Ala Lys
        195                 200                 205

Leu Ile Arg Ser Arg Gln Thr Leu Glu Gly Glu Phe Ile Pro Leu His
    210                 215                 220

Gln Thr Asp Leu Ser Val Gly Phe Asp Thr Gly Asp Asp Arg Leu Phe
225                 230                 235                 240

Leu Val Ser Pro Leu Val Ile Ser His Glu Ile Asp Ala Ala Ser Pro
                245                 250                 255
```

```
Phe Trp Glu Ala Ser Arg Arg Ala Leu Glu Arg Asp Asp Phe Glu Ile
            260                 265                 270
Val Val Ile Leu Glu Gly Met Val Glu Ala Thr Gly Met Thr Cys Gln
        275                 280                 285
Ala Arg Ser Ser Tyr Leu Val Asp Glu Val Leu Trp Gly His Arg Phe
        290                 295                 300
Thr Ser Val Leu Thr Leu Glu Asp Gly Phe Tyr Glu Val Asp Tyr Ala
305                 310                 315                 320
Ser Phe His Glu Thr Phe Glu Val Pro Thr Pro Ser Cys Ser Ala Arg
                325                 330                 335
Glu Leu Ala Glu Ala Ala Arg Leu Asp Ala His Leu Tyr Trp Ser
            340                 345                 350
Ile Pro Ser Arg Leu Asp Glu Lys Val Glu Glu Gly Ala Gly Glu
            355                 360                 365
Gly Gly Arg Cys Gly Arg Trp Ser
        370                 375

<210> SEQ ID NO 7
<211> LENGTH: 1827
<212> TYPE: DNA
<213> ORGANISM: Rattus norvegicus

<400> SEQUENCE: 7
cagcgcttgg ctcctgcgcc tccgcttcgt gtttgaatct ggatctcccc tccgtattat      60
gtctgcactc cgaaggaaat tggggacga ttaccaggta gtgaccactt cgtccagcgg     120
ttcgggcttg cagccccagg ggccaggaca gggcccacag cagcagcttg tacccaagaa     180
gaaacggcag cggttcgtgg acaagaacgg tcggtgcaat gtgcagcacg gcaacctggg     240
cagcgagacc agtcgctacc tttccgacct cttcactacc ctggtggatc tcaagtggcg     300
ttggaaacctc tttatcttca tcctcaccta caccgtggcc tggctcttca tggcgtccat     360
gtggtgggtg atcgcttata cccggggcga cctgaacaaa gcccatgtcg caactacac     420
tccctgtgtg gccaatgtct ataacttccc ctctgccttc cttttcttca tcgagaccga     480
ggccaccatc ggctatggct accgctacat caccgacaag tgccccgagg gcatcatcct     540
tttcctttc cagtccatcc ttggctccat cgtggacgct ttcctcatcg gctgcatgtt     600
catcaagatg tcccagccca aaagcgcgc cgagaccctc atgtttagcg agcatgcggt     660
tatttccatg agggacggaa aactcactct catgttccgg gtgggcaacc tgcgcaacag     720
ccacatggtc tccgcgcaga tccgctgcaa gctgctcaaa tctcggcaga cacctgaggg     780
tgagtttcta ccccttgacc aacttgaact ggatgtaggt tttagtacag ggcagatca     840
acttttcctt gtgtcccctc tcaccatttg ccacgtgatt gatgccaaaa gcccctttta     900
tgacctatcc cagcgaagca tgcaaactga acagttcgag gtggtcgtca tcctggaagg     960
catcgtggaa accacaggga tgacttgtca agctcgaaca tcatacaccg aagatgaagt    1020
tcttggggt catcgttttt tccctgtaat ttctttagaa gaaggattct ttaaagtcga    1080
ttactcccag ttccatgcaa cctttgaagt ccccacccct ccgtacagtg tgaaagagca    1140
ggaagaaatg cttctcatgt cttcccctt aatagcacca gccataacca acagcaaaga    1200
aagacacaat tctgtggagt gcttagatgg actagatgac attagcacaa aacttccatc    1260
gaagctgcag aaaattacgg ggagagaaga ctttcccaaa aaactcctga ggatgagttc    1320
tacaacttca gaaaaagcct atagtttggg tgatttgccc atgaaactcc aacgaataag    1380
```

| | |
|---|---|
| ttcggttcct ggcaactctg aagaaaaact ggtatctaaa accaccaaga tgttatcaga | 1440 |
| tcccatgagc cagtctgtgg ccgatttgcc accgaagctt caaaagatgg ctggaggacc | 1500 |
| taccaggatg gaagggaatc ttccagccaa actaagaaaa atgaactctg accgcttcac | 1560 |
| atagcaaaac accccattag gcattatttc atgttttgat ttagttttag tccaatattt | 1620 |
| ggctgataag ataatcctcc ccgggaaatc tgagaggtct atcccagtct ggcaaattca | 1680 |
| tcagaggact cttcattgaa gtgttgttac tgtgttgaac atgagttaca aagggaggac | 1740 |
| atcataagaa agctaatagt tggcatgtat tatcacatca agcatgcaat aatgtgcaaa | 1800 |
| ttttgcattt agttttctgg catgatt | 1827 |

<210> SEQ ID NO 8
<211> LENGTH: 2070
<212> TYPE: DNA
<213> ORGANISM: Rattus norvegicus

<400> SEQUENCE: 8

| | |
|---|---|
| ggcacgagaa tctggatctc ccctccgtat tatgtctgca ctccgaagga aatttgggga | 60 |
| cgattaccag gtagtgacca cttcgtccag cggttcgggc ttgcagcccc aggggccagg | 120 |
| acagggccca cagcagcagc ttgtacccaa gaagaaacgg cagcggttcg tggacaagaa | 180 |
| cggtcggtgc aatgtgcagc acggcaacct gggcagcgag accagtcgct accttttccga | 240 |
| cctcttcact accctggtgg atctcaagtg gcgttggaac ctctttatct tcatcctcac | 300 |
| ctacaccgtg gcctggctct tcatggcgtc catgtggtgg gtgatcgctt atacccgggg | 360 |
| cgacctgaac aaagcccatg tcggcaacta cactccctgt gtggccaatg tctataactt | 420 |
| cccctctgcc ttccttttct tcatcgagac cgaggccacc atcggctatg ctaccgcta | 480 |
| catcaccgac aagtgccccg agggcatcat ccttttcctt ttccagtcca tccttggctc | 540 |
| catcgtggac gctttcctca tcggctgcat gttcatcaag atgtcccagc ccaaaaagcg | 600 |
| cgccgagacc ctcatgttta gcgagcatgc ggttatttcc atgagggacg gaaaactcac | 660 |
| tctcatgttc cgggtgggca acctgcgcaa cagccacatg gtctccgcgc agatccgctg | 720 |
| caagctgctc aaatctcggc agacacctga gggtgagttt ctacccttg accaacttga | 780 |
| actggatgta ggttttagta caggggcaga tcaactttt cttgtgtccc ctctcaccat | 840 |
| ttgccacgtg atcgatgcca aaagcccctt ttatgaccta tcccagcgaa gcatgcaaac | 900 |
| tgaacagttc gaggtggtcg tcatcctgga aggcatcgtg gaaaccacag ggatgacttg | 960 |
| tcaagctcga acatcataca ccgaagatga agttctttgg ggtcatcgtt tttccctgt | 1020 |
| aatttcttta gaagaaggat tctttaaagt cgattactcc cagttccatg caacctttga | 1080 |
| agtccccacc cctccgtaca gtgtgaaaga gcaggaagaa atgcttctca tgtcttcccc | 1140 |
| tttaatagca ccagccataa ccaacagcaa agaaagacac aattctgtgg agtgcttaga | 1200 |
| tggactagat gacattagca caaaacttcc atcgaagctc cagaaaatta cggggagaga | 1260 |
| agactttccc aaaaaactcc tgaggatgag ttctacaact tcagaaaaag cctatagttt | 1320 |
| gggtgatttg cccatgaaac tccaacgaat aagttcggtt cctggcaact ctgaagaaaa | 1380 |
| actggtatct aaaaccacca agatgttatc agatcccatg agccagtctg tggccgattt | 1440 |
| gccaccgaag cttcaaaaga tggctggagg acctaccagg atggaaggga tcttccagc | 1500 |
| caaactaaga aaaatgaact ctgaccgctt cacatagcaa acaccccat taggcattat | 1560 |
| ttcatgtttt gatttagttt tagtccaata tttggctgat aagataatcc tccccgggaa | 1620 |
| atctgagagg tctatcccag tctggcaaat tcatcagagg actcttcatt gaagtgttgt | 1680 |

```
tactgtgttg aacatgagtt acaaagggag gacatcataa gaaagctaat agttggcatg   1740
tattatcaca tcaagcatgc aataatgtgc aaattttgca tttagttttc tggcatgatt   1800
tatatatggc atatttatat tgaatattct ggaaaaatat ataaatatat atttgaagtg   1860
gagatattct ccccataatt tctaatatat gtattaagcc aaacatgagt ggatagcttt   1920
cagggcacta aaataatata catgcataca tacatacatg catatgcaca gacacataca   1980
cacacatact catatatata aaacataccc atacaaacat atatatctaa taaaaattgt   2040
gatgttttgt tcaaaaaaaa aaaaaaaaaa                                   2070

<210> SEQ ID NO 9
<211> LENGTH: 2111
<212> TYPE: DNA
<213> ORGANISM: Rattus norvegicus

<400> SEQUENCE: 9
ggcacgaggg tttggagcgc ttggctcctg cgcctccgct tcgcgtttga atctggatct     60
cccctccgta ttatgtctgc actccgaagg aaatttgggg acgattacca ggtagtgacc    120
acttcgtcca gcggttcggg cttgcagccc caggggccag gacagggccc acagcagcag    180
cttgtaccca agaagaaacg gcagcggttc gtggacaaga acggtcggtg caatgtgcag    240
cacggcaacc tgggcagcga gaccagtcgc tacctttccg acctcttcac tacccctggtg   300 gatctcaagt ggcgttggaa cctctttatc ttcatcctca cctacaccgt ggcctggctc    360
ttcatggcgt ccatgtggtg ggtgatcgct tatacccggg gcgacctgaa caaagcccat    420
gtcggcaact acactccctg tgtggccaat gtctataact tccctctgc cttccttttc     480 ttcatcgaga ccgaggccac catcggctat ggctaccgct acatcaccga caagtgcccc    540
gagggcatca tccttttcct tttccagtcc atccttggct ccatcgtgga cgctttcctc    600
atcggctgca tgttcatcaa gatgtcccag cccaaaaagc gcgccgagac cctcatgttt    660
agcgagcatg cggttatttc catgagggac ggaaaactca ctctcatgtt ccgggtgggc    720
aacctgcgca cagccacat ggtctccgcg cagatccgct gcaagctgct caaatctcgg    780
cagacacctg agggtgagtt ctacccctt gaccaacttg aactggatgt aggttttagt    840
acaggggcag atcaactttt tcttgtgtcc cctctcacca tttgccacgt gatcgatgcc    900
aaaagcccct tttatgacct atcccagcga agcatgcaaa ctgaacagtt cgaggtggtc    960
gtcatcctgg aaggcatcgt ggaaaccaca gggatgactt gtcaagctcg aacatcatac   1020
accgaagatg aagttctttg gggtcatcgt ttttttccctg taatttcttt agaagaagga   1080
ttctttaaag tcgattactc ccagttccat gcaacctttg aagtccccac ccctccgtac   1140
agtgtgaaag agcaggaaga aatgcttctc atgtcttccc ctttaatagc accagccata   1200
accaacagca agaaagaca caattctgtg gagtgcttag atggactaga tgacattagc   1260
acaaaacttc catcgaagct gcagaaaatt acggggagag aagactttcc caaaaaactc   1320
ctgaggatga gttctacaac ttcagaaaaa gcctatagtt tgggtgattt gcccatgaaa   1380
ctccaacgaa taagttcggt tcctggcaac tctgaagaaa aactggtatc taaaaccacc   1440
aagatgttat cagatcccat gagccagtct gtggccgatt tgccaccgaa gcttcaaaag   1500
atggctggag gacctaccag gatggaaggg aatcttccag ccaaactaag aaaaatgaac   1560
tctgaccgct tcacatagca aaacaccca ttaggcatta tttcatgttt tgatttagtt     1620
ttagtccaat atttggctga taagataatc ctccccggga aatctgagag gtctatccca    1680
```

-continued

| | |
|---|---|
| gtctggcaaa ttcatcagag gactcttcat tgaagtgttg ttactgtgtt gaacatgagt | 1740 |
| tacaaaggga ggacatcata agaaagctaa tagttggcat gtattatcac atcaagcatg | 1800 |
| caataatgtg caaattttgc atttagtttt ctggcatgat ttatatatgg catatttata | 1860 |
| ttgaatattc tggaaaaata tataaatata tatttgaagt ggagatattc tccccataat | 1920 |
| ttctaatata tgtattaagc caaacatgag tggatagctt tcagggcact aaaataatat | 1980 |
| acatgcatac atacatacat gcatatgcac agacacatac acacacatac tcatatatat | 2040 |
| aaaacatacc catacaaaca tatatatcta ataaaaattg tgatgttttg ttcaaaaaaa | 2100 |
| aaaaaaaaaa a | 2111 |

<210> SEQ ID NO 10
<211> LENGTH: 1679
<212> TYPE: DNA
<213> ORGANISM: Mus musculus

<400> SEQUENCE: 10

| | |
|---|---|
| ctgcgcctcc gcttcgtgtt tgaatctggc tcgcccctcc gtattatgtc tgcactccga | 60 |
| aggaaatttg gggacgatta ccaggtagtg accacttcgt cgagcggttc gggcttacag | 120 |
| cctcagggc caggacaggg cccgcagcag cagctggtgc caagaagaa acggcagcgg | 180 |
| ttcgtggaca agaacggccg gtgcaatgtg cagcatggta acctgggcag cgagaccagt | 240 |
| cgctaccttt cggacctctt cactaccctg gtggatctca gtggcgttg gaacctcttt | 300 |
| atcttcatcc tcacctacac cgtggcctgg ctcttcatgg cgtccatgtg gtgggtgatc | 360 |
| gcttataccc ggggcgacct gaacaaagcc catgtcggca actacactcc ctgtgtggcc | 420 |
| aatgtctata acttcccctc tgccttcctc ttcttcatcg agaccgaggc caccatcggc | 480 |
| tatggctacc gctacatcac agataagtgc cccgagggca tcatcctctt cctcttccag | 540 |
| tccatccttg gctccatcgt ggacgctttc ctcatcggct gcatgttcat caagatgtcc | 600 |
| cagcccaaaa agcgcgccga gaccctcatg tttagcgagc atgcggttat ctccatgagg | 660 |
| gacggaaaac tcactctcat gttccgggtg ggcaacctgc gcaacagcca catggtctcc | 720 |
| gcgcagatcc gctgcaagct gctcaaatct cggcagacac tgagggtga gttccttccc | 780 |
| cttgaccaac ttgaactgga tgtaggtttt agtacagggg ccgatcaact ttttcttgtg | 840 |
| tccctctca caatttgcca cgtgatcgat gccaaaagcc ccttctatga cctatcccag | 900 |
| cgaagcatgc aaactgaaca gttcgaggtt gtcgtcatcc tggaaggcat tgtggaaacc | 960 |
| acaggaatga cttgtcaagc tcgaacatca tacacagagg acgaagtgct ttgggtcat | 1020 |
| cgttttttcc ctgtaatttc tttagaagaa ggattctta aagtcgatta ctcccagttc | 1080 |
| catgcaacct tgaagttcc aaccctcct tacagcgtga agagcagga ggaaatgctt | 1140 |
| ctcatgtcct ccccttttaat agcaccagcc ataaccaaca gcaaagaaag acacaattct | 1200 |
| gtggagtgtt tagatggact agatgacatt agcacaaaac ttccatcgaa gctgcagaaa | 1260 |
| attacgggga gagaagactt tccccaaaaaa cttctgagaa tgagttctac aacctcagaa | 1320 |
| aaagcctata gtttgggtga tttgcccatg aaactccaac gaataagttc agttcctggc | 1380 |
| aactcggaag aaaaactggt ttctaaaacc accagatgt tatctgatcc catgagccag | 1440 |
| tctgtggccg atttgccacc aaagcttcaa agatggctg aggacctac aggatggaa | 1500 |
| ggaaatcttc cagccaaact aagaaaaatg aactctgacc gtttcacata gcaaacacc | 1560 |
| cctttaggca ttatttaatg ttttgattta gtattagtcc aatatttggc tgataagata | 1620 |
| atcctcccta tgaaatctga gaggtctatc ctagcctggc aaatagatca gagaactct | 1679 |

<210> SEQ ID NO 11
<211> LENGTH: 2074
<212> TYPE: DNA
<213> ORGANISM: Homo sapiens

<400> SEQUENCE: 11

```
atggagtctc ctaacagcct ctcggtgctg atgtgaaatt tgaccatctg attccagttt      60
ttttcttttc cttttctttt ttgcatttcc ttccctcgcc atccgtcgtg tagtgaattg     120
ttcagtcttg ctccgtttca agagaggaga tcatgattga gtgaagccac cccgtccgca     180
gccaggaaaa gcacaaagaa gaaactgcaa caatggccaa gctgacagaa tccatgacta     240
acgtcctgga gggcgactcc atggatcagg acgtcgaaag cccagtggcc attcaccagc     300
caaagttgcc taagcaggcc agggatgacc tgccaagaca catcagccga gatcggacca     360
aaaggaaaat ccagaggtac gtgaggaaag acggaaagtg caatgttcat cacggcaacg     420
tgagggagac ctatcgctac ctgaccgata tcttcaccac attagtggac ctgaagtgga     480
gattcaacct attgattttt gtcatggttt acacagtgac ctggctcttt tttggaatga     540
tctggtggtt gatcgcatac atacggggag acatggacca catagaggac ccctcctgga     600
ctccttgtgt taccaacctc aacgggttcg tctctgcttt tttattctca atagagacag     660
aaaccaccat tggttatggc taccgggtca tcacagataa atgcccggag ggaattattc     720
ttctcttaat ccaatctgtg ttggggtcca ttgtcaatgc attcatggtg ggatgcatgt     780
ttgtaaaaat ctctcaaccc aagaagaggg cagagaccct ggtcttttcc acccatgcag     840
tgatctccat gcgggatggg aaactgtgcc tgatgttccg ggtaggggac cttaggaatt     900
cccacattgt ggaggcttcc atcagagcca agttgatcaa atccaaacag acctcggagg     960
gggagttcat cccgttgaac cagacggata tcaacgtagg gtattacacg ggggatgacc    1020
gtctgtttct ggtgtcaccg ctgatcatta gccatgaaat taaccaacag agtccttttct   1080
gggagatctc caaagcccag ctgcccaaag gaactggaa aattgtggtc atcctagaag    1140
gaatggtgga agccacaggg atgacatgcc aagctcgaag ctcctacatc accagtgaga    1200
tcctgtgggg ttaccggttc acacctgtcc tgaccctgga ggatgggttc acgaagttg    1260
actacaacag cttccatgag acctatgaga ccagcacccc atcccttagt gccaagagc    1320
tggccgagtt agccagcagg gcagagctgc ccctgagttg gtctgtatcc agcaaactca    1380
accaacatgc agaactggag actgaagagg aagaaaagaa cctcgaagag caaacagaaa    1440
gaaatggtga tgtggcaaac ctggagaatg aatccaaagt ttagtgccct agctgggcaa    1500
accttctct tctcccccca acacaatctt tccttgtctc tcattctctt tcttttttctg    1560
tctctcttgc tttgttcttt atttgtttat atttaatttt tacatgacca gaaaacaaat    1620
cttcaaggtg taaatatct acctgccctc tctcagttat tcagattgac aaggtagaca    1680
tggatttgat gaaagtgcaa agtgccctca tttgtggccc aagcctggtc tcctcccaaa    1740
atactacaca tccaactcct ggagatttca gttacttacc tgcatgtgtt gtacaatacc    1800
agatcactca aaaaggtgtg tcaaagattt tacctgggat atgacaagca aggtttctgg    1860
tgcctatta ttcattcagt gagacacaga gtggagccct cagttttatg gatcccaatt    1920
catttcatct actacagggt gaggtgcttg ccccccatgtg ggtgtggcag ttacagggcc    1980
caggtgagct gaagacaaac cactgtacat atatatgcct tatgtaatta ttttcttttt    2040
gtaattagta ataaaaccca gcatgtacaa aagt                                2074
```

<210> SEQ ID NO 12
<211> LENGTH: 2267
<212> TYPE: DNA
<213> ORGANISM: Mus musculus

<400> SEQUENCE: 12

| | | | | | | |
|---|---|---|---|---|---|---|
| ctgagctgcc | gttacattca | ggagaaacag | cagtgtcggc | ggctcccaat | ctcagaggga | 60 |
| acctagggta | ctgggggaga | tggtgtcagg | gacatggacg | ccaaccccca | agggtttctg | 120 |
| ctgctggcta | ctcttctctc | caggctctac | ttctgttcat | acggtccata | tctcctaggg | 180 |
| gaccctgaaa | gcctaggaac | cgactctggc | catccatctc | tccgggaaga | ttataaccca | 240 |
| gagtgcttct | caggggggaa | gaatttgaag | caaaaccaga | cccccgcagga | tccccgctgc | 300 |
| ggccgccatg | gcgcaggaga | cgccgctttt | ctctcccggg | tcggaggagc | cgccacgccg | 360 |
| ccgcggtcgc | cagcgctacg | tggagaagga | cggtcgctgt | aacgtgcagc | agggcaacgt | 420 |
| ccgcgagacc | taccgctacc | tgaccgacct | gttcaccacg | ctggtggacc | tgcagtggcg | 480 |
| cctcagactg | ctcttcttcg | tgctcgccta | cgcgctcact | tggctcttct | cggtgtcat | 540 |
| ctggtggctc | atcgcctacg | tcgcggcga | cctggagcac | ctggaggaca | ccgcgtggac | 600 |
| cccgtgcgtc | aacaacctca | acggcttcgt | ggccgccttc | ctcttctcca | tcgagacgga | 660 |
| gaccaccatc | ggctatgggc | accgcgtcat | caccgaccag | tgtcccgagg | gcatcgtgct | 720 |
| gctgctgctg | caggctatcc | tgggctccat | ggtgaacgct | ttcatggtgg | gctgcatgtt | 780 |
| cgtcaagatc | tcgcagccca | caagcgcgc | cgccactctc | gtcttctcct | cgcacgccgt | 840 |
| ggtgtctctg | cgcgacgggc | gcctctgtct | catgtttcgc | gtgggcgacc | tgcgatcctc | 900 |
| acacatcgtc | gaggcctcca | tccgagccaa | gctcatccgc | tcccgtcaga | cgctcgaggg | 960 |
| cgagttcatc | cctttgcacc | agaccgacct | cagcgtgggc | tttgacacgg | ggacgaccg | 1020 |
| cctctttctc | gtctcacctc | tcgtcatcag | ccacgaaatc | gatgccgcca | gccccttctg | 1080 |
| ggaggcatcg | cgccgcgccc | tcgagaggga | cgacttcgag | atcgtagtca | ttctcgaggg | 1140 |
| catggtggag | gccacgggaa | tgacgtgcca | agctcgaagc | tcgtacctgg | tggatgaagt | 1200 |
| gttgtgggga | caccggttca | catccgtgct | caccctggag | gatggtttct | atgaggtgga | 1260 |
| ctacgccagc | ttccacgaaa | cctttgaggt | gcccacaccc | tcgtgcagtg | ctcgggaact | 1320 |
| ggcagaagcc | gcggcccgcc | ttgatgccca | tctctactgg | tccatcccca | gcaggctgga | 1380 |
| tgagaaggtg | gaggaagaag | gggctgggga | gggggcagg | tgcgggagat | ggagctgaca | 1440 |
| aggagcacaa | tggctgccac | ccccagagag | tgagtccaag | gtgtgactgg | tttcctccca | 1500 |
| ccccctgtgg | cagaccaggg | ggccggactc | aggtacacag | aagctgcgag | tggaggtgga | 1560 |
| agaagaggag | gcaggcagtg | tcccgaggaa | cagctaaagt | tgggagaggc | ccgctgagtc | 1620 |
| caggatcgag | tagggaaggc | tgaggtcctg | gtttgaagag | agagggttgc | agggcggggt | 1680 |
| gagagaacat | gtcagtctgt | ctgtgtttga | ccttcacatc | ggttcatggg | tggatggatg | 1740 |
| gacagaagga | tgggctcatg | ggggttgatc | gggaaggtgg | agcagataga | gacagccaat | 1800 |
| ggataatcgc | tcaggtggta | agtggcttgg | cagtcgatga | tcgtcacctg | cagcacacct | 1860 |
| ttgtgagaaa | tccatgggca | tccttttctt | ccagatatag | gtagcctcaa | accagggagc | 1920 |
| gtggcttagg | gagcaggctg | tcaggtggac | taccaccccc | actcacctcc | cctcaactgg | 1980 |
| cctccctgat | gtgtgacacg | cctgcctaac | tagagaagag | agcactgggt | agaggtggac | 2040 |
| acaggtgtgg | ctgccctccc | cagtatcact | gtcccatggc | gagaggtcag | aaaggcaaac | 2100 |
| aaacaatggg | ggtagatgct | gagcagggag | gggccctgaa | gcaggacctg | gggacagcca | 2160 |

| | |
|---|---|
| aggacaacta ttttgtgaga gaggaatgaa accttgcagg tcctgccaca gaagcaagaa | 2220 |
| gcagaggaaa ggccatggag agacttaata aagggtttta caaggga | 2267 |

<210> SEQ ID NO 13
<211> LENGTH: 1260
<212> TYPE: DNA
<213> ORGANISM: Rattus norvegicus

<400> SEQUENCE: 13

| | |
|---|---|
| atggccggtg attctaggaa tgctatgaat caagacatgg ataggagt cacctcccag | 60 |
| gaccacaaga agatccccaa acaggctcgg gattacatcc ccattgccac agaccgcact | 120 |
| cgcctgctgc cggaaggcaa gaagccacgc cagcgctaca tggagaagac cggcaagtgt | 180 |
| aacgtgcacc atggcaatgt tcaggaaacc taccgctacc taagtgacct cttcaccacc | 240 |
| ctggtggacc tcaaatggcg cttcaacctt ctggtcttca ccatggtcta caccattact | 300 |
| tggctattct ttggcttcat ctggtggctc attgcttatg tccgaggtga tctggaccac | 360 |
| gtgggtgacc aagagtggat cccttgtgtt gaaaaccta gtggctttgt gtctgctttc | 420 |
| ctgttctcca ttgagacaga aacaaccatt gggtatggct tcagagtcat tacagagaag | 480 |
| tgtccagagg ggatcattct ccttctagtg caggccatcc tggctctat tgttaatgcc | 540 |
| ttcatggtgg gttgcatgtt tataaagatc agccagccaa agaagagagc agagaccctc | 600 |
| atgttctcca acaatgctgt catctccatg cgggatgaga agctgtgcct catgttccgg | 660 |
| gtagggacc tccgaaactc ccatatcgtg gaggcctcca tccgcgccaa gcttatcaag | 720 |
| tcccggcaga ccaaagaagg ggaattcatc cccttgaacc agaccgacat taacgtgggc | 780 |
| tttgacactg gtgacgaccg cctcttcctg gtgtcccccc tcatcatctc ccatgagatc | 840 |
| aatgagaaga gccctttctg ggagatgtct cgtgctcaac tggagcagga agagttcgag | 900 |
| gtcgtggtca tactagaagg gatggtagaa gccacaggca tgacttgcca agcacggagc | 960 |
| tcttacatgg atacagaggt gctctggggt caccgattca caccagtcct caccttggaa | 1020 |
| aagggcttct atgaggtgga ctacaacact ttccacgaca cctatgagac caacacaccc | 1080 |
| agctgctgtg ccaaggagct ggcagaaatg aagaggaatg gtgagctcct ccagtccttg | 1140 |
| cccagtcctc ctttgcttgg gggctgcgct gaggctgaga aagaagcaga ggctgagcac | 1200 |
| gatgaggagg aggaacccaa tggactgagt gtgtcccggg caacaagggg ctcaatgtga | 1260 |

<210> SEQ ID NO 14
<211> LENGTH: 3156
<212> TYPE: DNA
<213> ORGANISM: Rattus norvegicus

<400> SEQUENCE: 14

| | |
|---|---|
| gtttacacgc ctctgctagc tggacctgcg acaccagagt ggctcagggc ggctgtcggt | 60 |
| acgtaggcaa tgcctgaggc tatggaatcc cctggagagc cctgagagcc acacgcaccg | 120 |
| ccttgaaggg atcgccagaa gttagcccca agggttcaga gaagctctct gctctacgac | 180 |
| tatggccggt gattctagga atgctatgaa tcaagacatg gagataggag tcacctccca | 240 |
| ggaccacaag aagatcccca acaggctcg gattacatc cccattgcca gagaccgcac | 300 |
| tcgcctgctg ccggaaggca agaagccacg ccagcgctac atggagaaga ccggcaagtg | 360 |
| taacgtgcac catggcaatg ttcaggaaac ctaccgctac ctaagtgacc tcttcaccac | 420 |
| cctggtggac ctcaaatggc gcttcaacct tctggtcttc accatggtct acaccattac | 480 |

```
ttggctattc tttggcttca tctggtggct cattgcttat gtccgaggtg atctggacca      540
cgtgggtgac caagagtgga tcccttgtgt tgaaaacctt agtggctttg tgtctgcttt      600
cctgttctcc attgagacag aaacaaccat tgggtatggc ttcagagtca ttacagagaa      660
gtgtccagag gggatcattc tccttctagt gcaggccatc ctgggctcta ttgttaatgc      720
cttcatggtg ggttgcatgt tgtaaagat cagccagcca agaagagag cagagaccct       780 catgttctcc aacaatgctg tcatctccat gcgggatgag aagctgtgcc tcatgttccg      840
ggttggggac ctccgaaact cccatatcgt ggaggcctcc atccgcgcca agcttatcaa      900
gtcccggcag accaaagaag gggaattcat ccccttgaac cagaccgaca ttaacgtggg      960
ctttgacact ggtgacgacc gcctcttcct ggtgtccccc ctcatcatct cccatgagat     1020
caatgagaag agccctttct gggagatgtc tcgtgctcaa ctggagcagg aagagtttga     1080
ggttgtggtc atactagaag ggatggtaga agccacaggc atgacttgcc aagcacggag     1140
ctcttacatg gatacagagg tgctctgggg tcaccgattc acaccagtcc tcaccttgga     1200
aaagggcttc tatgaggtgg actacaacac tttccacgac acctatgaga ccaacacacc     1260
cagctgctgt gccaaggagc tggcagaaat gaagaggaat ggtcagctcc tccagtcctt     1320
gcccagtcct cctttgcttg ggggctgcgc tgaggctgag aaagaagcag aggctgagca     1380
cgatgaggag gaggaaccca atggactgag tgtgtcccgg caacaagggg ctcaatgtg      1440 aagcctgtgt gctacccaga gcctcttcct gtcagacacc aaggagcctg agaggccaga     1500
gaggcaatta gttgagcaag cttttgtggag tcccaggagt atgggacttc tacaaagagg     1560
aacagtgtgg tgaggcctcg catctcctcc tcagggcctc ggagcaagtg gcgttgacta     1620
ggcctcccaa gaagtgtttt ctcggcctct gtgaaggaga gcattagggg tcaccagggt     1680
gggcttccca aggaggagtt cttaggtgtc atccatcctc tctctgactg ctgaagcctg     1740
ctcactggcc tccctgattc tctgtttcct cagcacaatc actgaggcct gtgaatggag     1800
ggactaattc catccatgga tactcaggcc tccaactggg gatgagttca cagaggcctt     1860
ccaggggcaa tgccctgcag tctgaggcca aaacccactg atttaatagc ttcttagcaa     1920
ggccccttaa cctctgatac tacctactgt gtgttttcct cttctgtgtc ctcttccatg     1980
acactacggc ttacagggta attgatttaa ttagagtggc cctaggacac tgagtaccta     2040
ggagcacaca caatgtcgtc ctcacaactg cctggcactc ctactcacac ttcaaaggac     2100
agacacagca gttgtggctt tgtaggagt gtgtggcaaa agaacttcaa agaaccgacc      2160
tctaaagcgg tcccgggaa catgtgaatt tcagagagcc agattagctc attggtacta      2220
acatagggat ggcagacagg aaagagacac aaggataatt ttaaaataag tatctggagc     2280
ctggtgttgt gatgcatgcc tgtaatccta gcatttggca ggctgaggca gaattgagaa     2340
tttgaagcca gccgggctat atagccctgt ctgaaaaaag caagagacaa actacaacca     2400
aggaaacatc tgccacagtt gttgcatggg gctcctcgga gaaagtagg ctatgaaaca      2460 caagtgacaa gaggccataa aggcatcttc actgccaagc caagtgtgga ccagagtctt     2520
ggctgccgct gagatgcctc tgggcctcct ccctatggaa cagctccaac aggtggtggg     2580
acctagaggg aggtccctga gaacaggatg agaggttggt gggtgactag ggaaagaaga     2640
gtctaagtgt ggagcagagc cttggggtcc acagcctcag agacctttct cttccagtct     2700
aggagatctg atggtcggtc agtgaagcat tatgttgaaa acaaagttgg cctggtcttg     2760
ggaatatgct agcatgatcc ccaacaccte tacccgggtg ttcatggctc tcaaccagcc     2820
tctgagaata gaagcacctt cctgccaggc cctagagaac tttctctggc atctccaagg     2880
```

-continued

| | |
|---|---|
| agatgagacg ctaaggctag ggaacagcat cctaacctca ggccttgttc cccttacagg | 2940 |
| gtgcccaggt ctctaggctg gtgagaaggt gtcctaggat ggctagctac attgtggacc | 3000 |
| agacacagat agaacagggg aaccttgact tgttatctgg gctgaatctt gaaagacagt | 3060 |
| ctaaagccag tggttctcaa ccttcctaat gctgtgacct tttaatatag ttcctcatgt | 3120 |
| tgtgatgacc ccaatcataa aattattttt gttcct | 3156 |

<210> SEQ ID NO 15
<211> LENGTH: 1260
<212> TYPE: DNA
<213> ORGANISM: Homo sapiens

<400> SEQUENCE: 15

| | |
|---|---|
| atggctggtg attctaggaa tgccatgaac caggacatgg agattggagt cactccctgg | 60 |
| gaccccaaga agattccaaa acaggcccgc gattatgtcc ccattgccac agaccgtacg | 120 |
| cgcctgctgg ccgagggcaa gaagccacgc cagcgctaca tggagaagag cggcaagtgc | 180 |
| aacgtgcacc acggcaacgt ccaggagacc taccggtacc tgagtgacct cttcaccacc | 240 |
| ctggtggacc tcaagtggcg cttcaacttg ctcgtcttca ccatggttta cactgtcacc | 300 |
| tggctgttct tcggcttcat ttggtggctc attgcttata tccggggtga cctggaccat | 360 |
| gttggcgacc aagagtggat tccttgtgtt gaaaacctca gtggcttcgt gtccgctttc | 420 |
| ctgttctcca ttgagaccga aacaaccatt gggtatggct tccgagtcat cacagagaag | 480 |
| tgtccagagg ggattatact cctcttggtc caggccatcc tgggctccat cgtcaatgcc | 540 |
| ttcatggtgg ggtgcatgtt tgtcaagatc agccagccca agaagagagc ggagaccctc | 600 |
| atgttttcca caacgcagt catctccatg cgggacgaga gctgtgcct catgttccgg | 660 |
| gtgggcgacc tccgcaactc ccacatcgtg gaggcctcca tccgggccaa gctcatcaag | 720 |
| tcccggcaga ccaaagaggg ggagttcatc cccctgaacc agacagacat caacgtgggc | 780 |
| tttgacacgg gcgacgaccg cctcttcctg gtgtctcctc tgatcatctc ccacgagatc | 840 |
| aacgagaaga gccctttctg ggagatgtct caggctcagc tgcatcagga agagtttgaa | 900 |
| gttgtggtca ttctagaagg gatggtggaa gccacaggca tgacctgcca gcccggagc | 960 |
| tcctacatgg atacagaggt gctctggggc caccgattca caccagtcct caccttggaa | 1020 |
| aagggcttct atgaggtgga ctacaacacc ttccatgata cctatgagac caacacaccc | 1080 |
| agctgctgtg ccaaggagct ggcagaaatg aagagggaag gccggctcct ccagtacctc | 1140 |
| cccagccccc cactgctggg gcggtgtgct gaggcagggc tggatgcaga ggctgagcag | 1200 |
| aatgaagaag atgagcccaa ggggctgggt gggtccaggg aggccagggg ctcggtgtga | 1260 |

<210> SEQ ID NO 16
<211> LENGTH: 1349
<212> TYPE: DNA
<213> ORGANISM: Homo sapiens

<400> SEQUENCE: 16

| | |
|---|---|
| ggggtggggg tggcttccat cttgtgttct agtgaatcag aacagcccac ttcactgatg | 60 |
| gtgtcttttt aactcaaagc atcccagcta tggctggcga ttctaggaat gccatgaacc | 120 |
| aggacatgga gattggagtc actccctggg accccaagaa gattccaaaa caggcccgcg | 180 |
| attatgtccc cattgccaca gaccgtacgc gcctgctggc cgagggcaag aagccacgcc | 240 |
| agcgctacat ggagaagagc ggcaagtgca acgtgcacca cggcaacgtc caggagacct | 300 |

-continued

```
accggtacct gagtgacctc ttcaccaccc tggtggacct caagtggcgc ttcaacttgc    360
tcgtcttcac catggtttac actgtcacct ggctgttctt cggcttcatt tggtggctca    420
ttgcttatat ccggggtgac ctggaccatg ttggcgacca agagtggatt ccttgtgttg    480
aaaacctcag tggcttcgtg tccgctttcc tgttctccat tgagaccgaa acaaccattg    540
ggtatggctt ccgagtcatc acagagaagt gtccagaggg gattatactc ctcttggtcc    600
aggccatcct gggctccatc gtcaatgcct tcatggtggg gtgcatgttt gtcaagatca    660
gccagcccaa gaagagagcg gagaccctca tgttttccaa caacgcagtc atctccatgc    720
gggacgagaa gctgtgcctc atgttccggg tgggcgacct ccgcaactcc cacatcgtgg    780
aggcctccat ccgggccaag ctcatcaagt cccggcagac caagaggggg gagttcatcc    840
ccctgaacca gacagacatc aacgtgggtt ttgacacggg cgacgaccgc ctcttcctgg    900
tgtctcctct gatcatctcc cacgagatca acgagaagag ccctttctgg gagatgtctc    960
aggctcagct gcatcaggaa gagtttgaag ttgtggtcat tctagaaggg atggtggaag   1020
ccacaggcat gacttgccaa gcacggagct cttacatgga tacagaggtg ctctggggcc   1080
accgattcac accagtcctc accttggaaa agggcttcta tgaggtggac tacaacacct   1140
tccatgatac ctatgagacc aacacaccca gctgctgtgc caaggagctg gcagaaatga   1200
agagggaagg ccggctcctc cagtacctcc ccagccccc actgctgggg ggctgtgctg   1260
aggcagggct ggatgcagag gctgagcaga atgaagaaga tgagcccaag ggactgggtg   1320
ggtccaggga ggccaggggc tcggtgtga                                     1349
```